US008304273B2

(12) United States Patent
Stellacci et al.

(10) Patent No.: US 8,304,273 B2
(45) Date of Patent: Nov. 6, 2012

(54) INSULATED NANOGAP DEVICES AND METHODS OF USE THEREOF

(75) Inventors: Francesco Stellacci, Somerville, MA (US); J Robert Barsotti, Jr., Philadelphia, PA (US); Zhang Huijuan, Singapore (SG); John Thong, Singapore (SG)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/864,172

(22) PCT Filed: Jan. 23, 2009

(86) PCT No.: PCT/US2009/031754
§ 371 (c)(1),
(2), (4) Date: Nov. 17, 2010

(87) PCT Pub. No.: WO2009/131724
PCT Pub. Date: Oct. 29, 2009

(65) Prior Publication Data
US 2011/0056845 A1 Mar. 10, 2011

Related U.S. Application Data

(60) Provisional application No. 61/006,635, filed on Jan. 24, 2008.

(51) Int. Cl.
*H01L 21/00* (2006.01)
*G01N 15/06* (2006.01)
*G01N 33/00* (2006.01)
*G01N 33/48* (2006.01)

(52) U.S. Cl. ............ 438/49; 422/50; 422/83; 422/68.1; 438/22; 438/23; 438/24; 438/42; 438/48; 438/142

(58) Field of Classification Search .................... 422/50, 422/83, 68.1; 438/22, 23, 24, 42, 48, 49, 438/142
See application file for complete search history.

(56) References Cited

U.S. PATENT DOCUMENTS

| 6,791,338 B1 * | 9/2004 | Bratkovski et al. ........... 324/600 |
| 7,880,079 B2 * | 2/2011 | Tanielian ...................... 136/205 |
| 7,915,144 B2 * | 3/2011 | Tanielian ...................... 438/468 |

(Continued)

FOREIGN PATENT DOCUMENTS

WO WO2006/088425 A1 8/2006

(Continued)

OTHER PUBLICATIONS

Kronholz S. et al., "Protected nanoelectrodes of two different metals with 30nm gapwidth and access window," Microelectronic Engineering; 2006, vol. 83, pp. 1702-1705.

(Continued)

*Primary Examiner* — Brian J Sines
(74) *Attorney, Agent, or Firm* — Pearl Cohen Zedek Latzer, LLP; Mark S. Cohen

(57) ABSTRACT

The present invention provides a method to eliminate undesired parallel conductive paths of nanogap devices for aqueous sensing. The method involves the electrical insulation of an electrode pair, except for the nanogap region wherein electrical response is measured. The magnitude of undesired ionic current in a measurement is reduced by two orders of magnitude. The process to accomplish the present invention is self-aligned and avoids fabrication complexity. The invention has a great potential in nanogap device applications.

14 Claims, 21 Drawing Sheets

U.S. PATENT DOCUMENTS

| | | | |
|---|---|---|---|
| 2004/0135144 A1* | 7/2004 | Yamada et al. | 257/59 |
| 2004/0195934 A1* | 10/2004 | Tanielian | 310/306 |
| 2004/0229386 A1* | 11/2004 | Golovchenko et al. | 438/10 |
| 2007/0023077 A1* | 2/2007 | Tanielian | 136/201 |
| 2007/0137687 A1* | 6/2007 | Tanielian | 136/205 |
| 2007/0235826 A1* | 10/2007 | Jaiprakash et al. | 257/415 |
| 2010/0142259 A1* | 6/2010 | Drndic et al. | 365/158 |

FOREIGN PATENT DOCUMENTS

| | | |
|---|---|---|
| WO | WO2007/040558 | 4/2007 |

OTHER PUBLICATIONS

Verleger, S., "Fabrication of Metal Molecule Contacts," Diploma Thesis, University of Konstanz; Jun. 29, 2006—Whole document.

* cited by examiner a)

b)

| Heating time | area(nm$^2$) | Original volume (nm$^3$) | Final Volume (nm$^3$) | Volume lost(nm$^3$) |
|---|---|---|---|---|
| 1min | 1.1856e+007 | 9.6049e+008 | 7.2088e+008 | 2.4E+8 |
| 2min | 1.5052e+007 | 1.2918e+009 | 9.8945e+008 | 3.0E+8 |
| 3min | 1.6983e+007 | 1.6496e+009 | 1.2744e+009 | 3.8E+8 |
| 4min | 1.6782e+007 | 2.6994e+009 | 2.1711e+009 | 5.3E+8 |
| 5min | 1.9686e+007 | 4.1953e+009 | 3.4856e+009 | 7.1E+8 |

Table 1

INSULATED NANOGAP DEVICES AND METHODS OF USE THEREOF

CROSS-REFERENCE TO RELATED APPLICATIONS

This application is a National Phase Application of PCT International Application No. PCT/US09/31754, International Filing Date Jan. 23, 2009, claiming priority of U.S. Provisional Patent Applications, 61/006,635, filed Jan. 24, 2008, all of which are incorporated herein by reference in their entirety.

FIELD OF THE INVENTION

The present invention relates to nanogap devices, and methods of use thereof.

BACKGROUND OF THE INVENTION

Nanogap devices comprise pairs of electrodes with nanoscale spatial separation, which are capable of accommodating nano-objects, such as functionalized nanoparticles, nanowires and isolated molecules or molecular aggregates for electrical characterization and sensing applications.

Fabrication of nanogap devices has been of major interest, due to their promising application in nanotechnology. While nanogap devices have been utilized to electronically characterize nano-objects and molecules under a dry environment, studies conducted in aqueous solutions were limited by signal to noise issues. Electrical signal to noise ratios suffered from conduction through electrolyte solutions, where ionic currents are often many orders of magnitude greater than the current flowing through the object in the gap.

Measuring molecules and nano-sized materials electronically in a fluidic solution, however, is highly applicable for biological and chemical sensing, for nanoparticle detection and characterization and for catalysis and synthesis. Such devices can also find applications as switching and computing components in future electronic devices.

Devices and methods are needed that can accurately electronically probe nanostructures and molecules in solution. Such devices should allow for the detection of an electrical signal, which is not perturbed by background signals from the solution.

SUMMARY OF THE INVENTION

In one embodiment, this invention provides a nanogap device for measuring changes in electrical properties or electrical responses of a sub-micron sized material. The nanogap device comprises a substrate and at least one conducting electrode pair separated by a nanogap positioned on or within the substrate. The first portion of the conducting electrode pair comprises an insulator coating; and the second portion of the conducting electrode pair, which is proximal to the nanogap, does not comprise an insulator coating.

In one embodiment, the nanogap has a width ranging from between 0.5-100 nm. In one embodiment, the second portion of the conducting electrode pair has a size ranging from between 0.01% to 1% of the total electrode area.

In one embodiment, the electrode pair is comprised of any conductive material, which in one embodiment is gold. In one embodiment, the insulator coating comprises a polymer, which in one embodiment is PolyMethylMethacrylate (PMMA). In one embodiment, the substrate comprises silicon, silicon dioxide, or a combination thereof.

In one embodiment, the nanogap device comprises an array of electrode pairs.

In one embodiment, the device is compatible for use with a liquid or a gas.

In one embodiment, the device size ranges from between 100 nm to 10 cm. In one embodiment, the electrode pair comprises a conducting wire, which is suspended over the substrate. In one embodiment, the device is comprised of a biocompatible material.

In one embodiment, this invention provides an apparatus comprising a nanogap device. In one embodiment, the apparatus comprising a power supply and a conductance measuring system operationally connected to the nanogap device. In one embodiment, the apparatus is comprising a unit to induce fluid flow in the nanogap device.

In one embodiment this invention provides a process for preparing a nanogap device. In one embodiment the process comprising: positioning a conducting wire on a substrate, wherein said conducting wire comprises a second portion that is thinner than a first portion of the wire; applying an insulator coating to said conducting wire; and applying a voltage to said conducting wire. Application of voltage results in electromigration of atoms in the second thinner portion forming a gap in that portion. Application of voltage also causes heating of the second thinner portion, resulting in at least partial removal of the insulator coating in that thinner portion.

According to this aspect of the invention and in some embodiments, the electromigration of atoms occurs after at least partial removal of said insulator coating. In one embodiment, the electromigration of atoms and the at least partial removal of said insulator coating are parallel processes. In one embodiment, the nanogap formed has a width ranging from between 0.5-100 nm. In one embodiment, the removal of insulator coating results in an uncoated area ranging between 0.01% to 1% of the total area of the conducting wire.

In one embodiment, the conducting wire is made of gold. In one embodiment, the insulating coating is PolyMethylMethacrylate (PMMA). In one embodiment, the substrate is silicon, silicon dioxide or a combination thereof.

In one embodiment, the process includes preparing a device comprising an array of electrode pairs.

In one embodiment the process comprises a device which is compatible for use with a liquid or a gas. In one embodiment the process comprising a device size, ranges from between 100 nm to 10 cm. In one embodiment the process comprising at least the thin portion of the conducting wire suspended over the substrate. In one embodiment the process provides a device comprised of a biocompatible material.

In one embodiment this invention provides a process for measuring electrical properties or an electrical response of a sub-micron sized object. According to this aspect and in one embodiment the process comprises placing a sub-micron sized material within a nanogap device. The nanogap device comprises a substrate, at least one conducting electrode pair separated by a nanogap positioned on or within the substrate, wherein the first portion of the conducting electrode pair comprises an insulator coating; and the second portion of the conducting electrode pair proximal to the nanogap does not comprise an insulator coating. The nanogap device further comprises a power supply operationally connected to the electrode pair. The sub-micron sized object is placed within or proximal to the nanogap.

Upon application of a voltage, an electrical response of the sub-micron sized material is measured in the device.

In one embodiment this invention provides a method for specific sensing of a molecule of interest. According to this aspect and in one embodiment the method comprises placing a sub-micron sized material within a nanogap device comprising a substrate and at least one conducting electrode pair separated by a nanogap positioned on or within said substrate. The first portion of the conducting electrode pair comprises an insulator coating, and the second portion of the conducting electrode pair proximal to the nanogap does not comprise an insulator coating. The method further comprises a power supply operationally connected to said electrode pair. The sub-micron sized material is placed within or proximal to the nanogap.

The method further comprises applying a voltage to the device and measuring an electrical response of the sub-micron sized material placed in the nanogap of the device.

In some embodiments the sub-micron sized material comprises a targeting moiety. According to this aspect and in some embodiments the method further comprises the introduction of a fluid comprising a molecule of interest specifically interacting with, or suspected of specifically interacting with the targeting moiety.

The specific interaction between the molecule of interest and the targeting moiety causes a change in the electrical response of the sub-micron sized material. This change in electrical response is detected and/or measured, and in some embodiments this detected or measured change serves as an indicator for specific sensing of the molecule of interest.

In one embodiment this invention provides a process for electrically manipulating a sub-micron sized object. The process comprises placing a sub-micron sized material within a nanogap device comprising a substrate and at least one conducting electrode pair separated by a nanogap positioned on or within said substrate. The conducting electrode pair comprises a first portion comprising an insulator coating; and a second portion, proximal to the nanogap, that does not comprise an insulator coating. The sub-micron sized material is placed proximal to the nanogap.

According to some embodiments the method further comprises applying voltage to the device whereby application of the voltage results in a change in electronic configuration of the sub-micron sized material, causing an electrical manipulation of the sub-micron sized material.

According to this aspect and in some embodiments, the change in electronic configuration induces a chemical change, a structural change, a conformational change, a binding event or a combination thereof in the sub-micron sized material.

Figure 15:
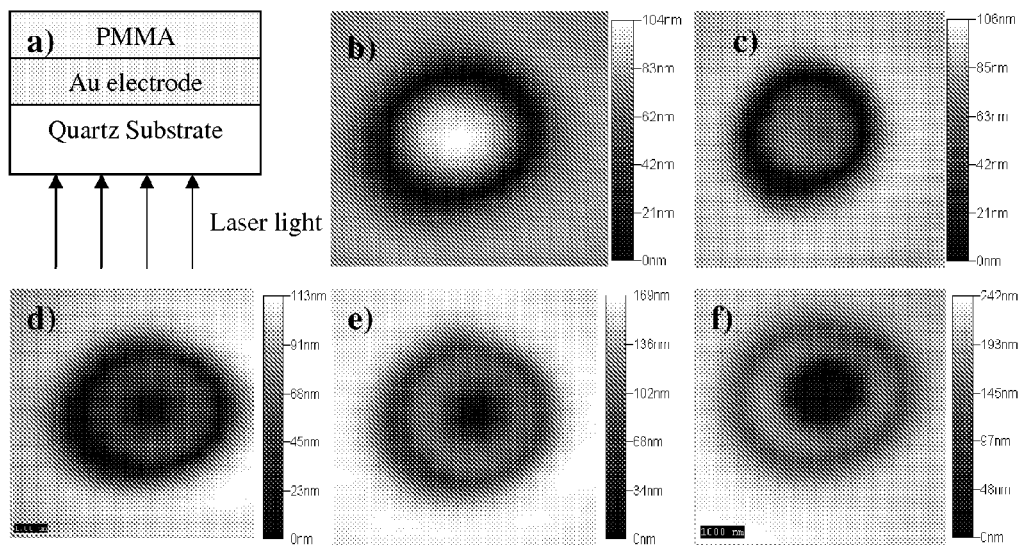
FIG. 15 depicts a) an embodiment of laser heating of PMMA layer; gradual topographical change of a PMMA layer heated by a laser at t=b) 1 min; c) 2 mins; d) 3 mins; e) 4 mins; f) 5 mins.

Table 1 demonstrates volume calculation of the polymer layer as shown in FIG. 15 using MATLAB.

Figure 16:
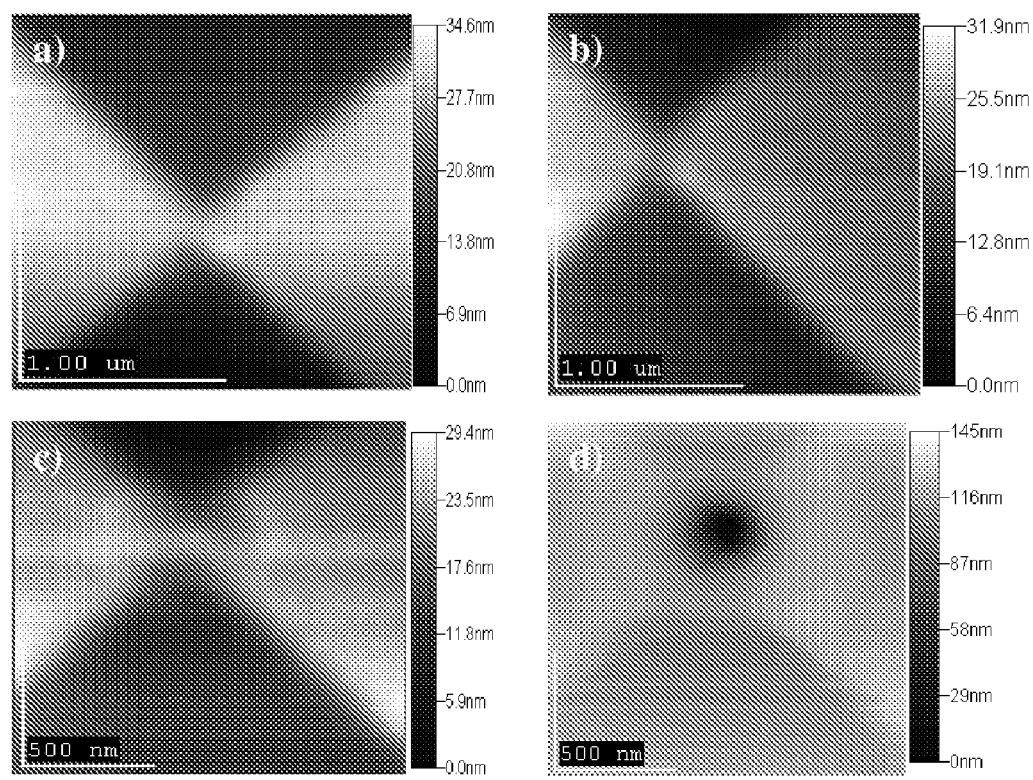

FIG. 16 depicts an embodiment of in situ AFM image of a butterfly electrode coated with PMMA at a) t=0; b) t=100 mins; c) t=135 mins; d) final image t=136 mins.

Figure 17:
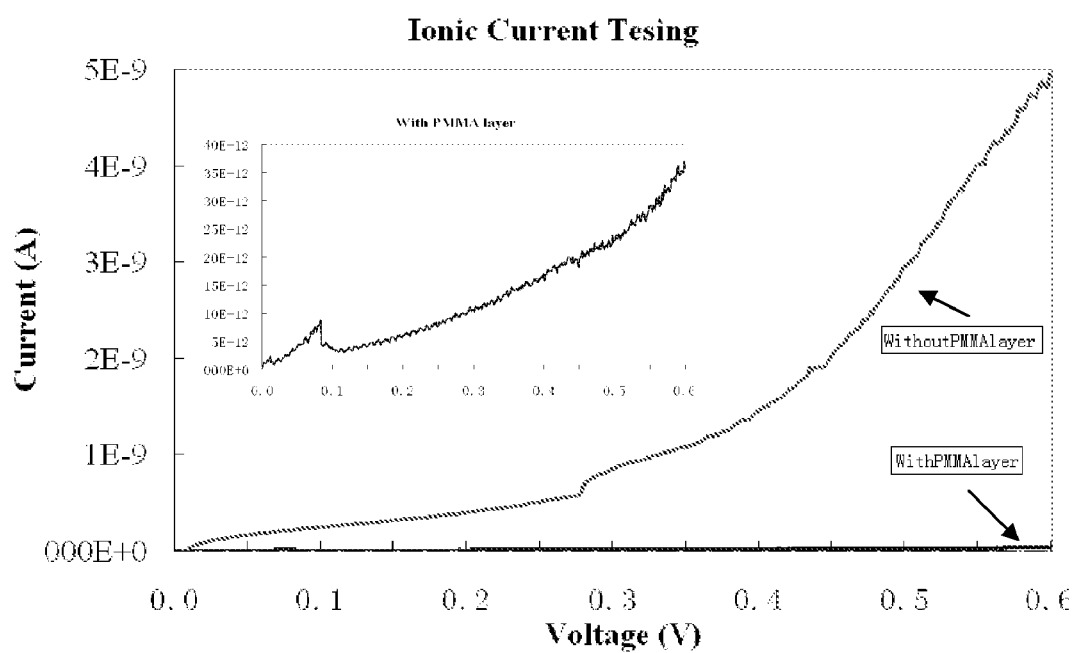

FIG. 17 depicts an embodiment of test results of 0.1M $CaCl_2$: IV curve of a nanogap without insulating layer and a nanogap with insulating layer.

Figure 18:
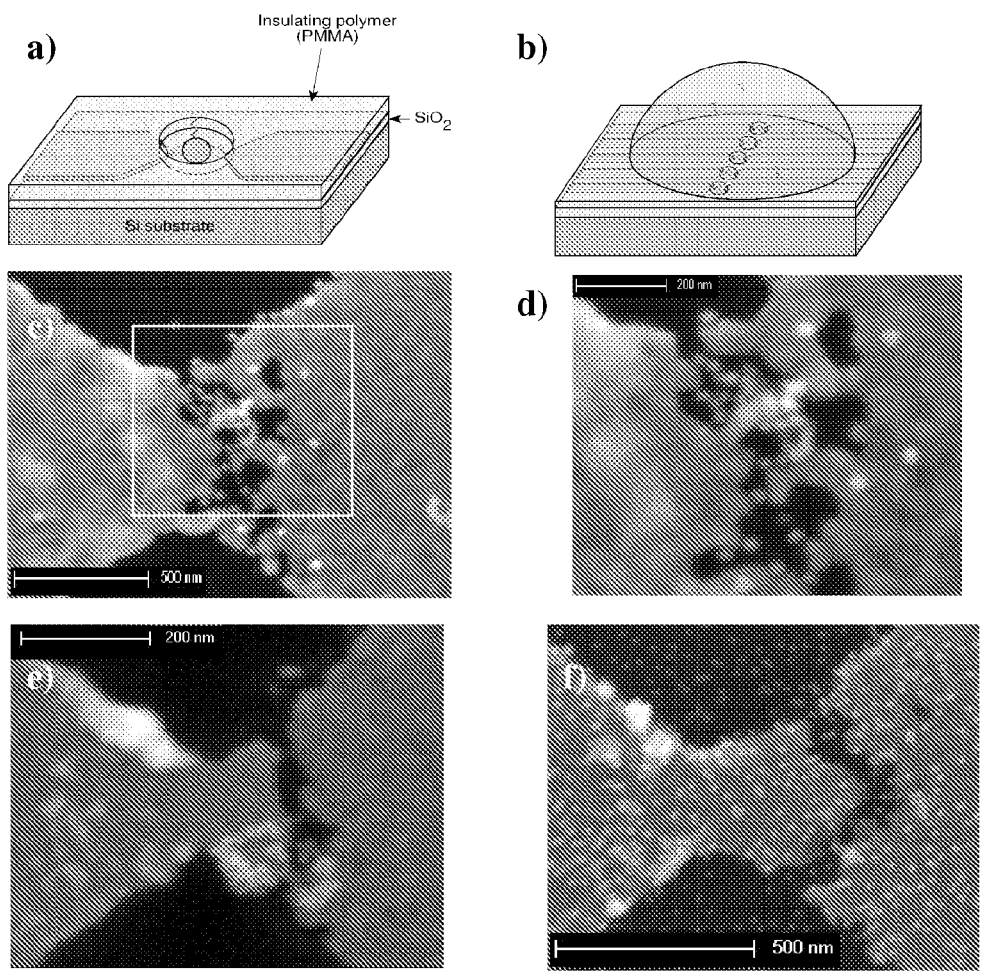

FIG. 18 depicts schematic drawing of a) a nanoparticle-in-nanogap biosensor; b) multigaps with different types of nanoparticle sensors; c) a SEM picture of nanoparticles deposited by dielectrophoresis; d) magnified picture of c); e) selective gold nanoparticle deposition by direct chemical assembly; d) gold nanoparticle deposition by direct chemical assembly to a bare Nanogap.

Figure 19:
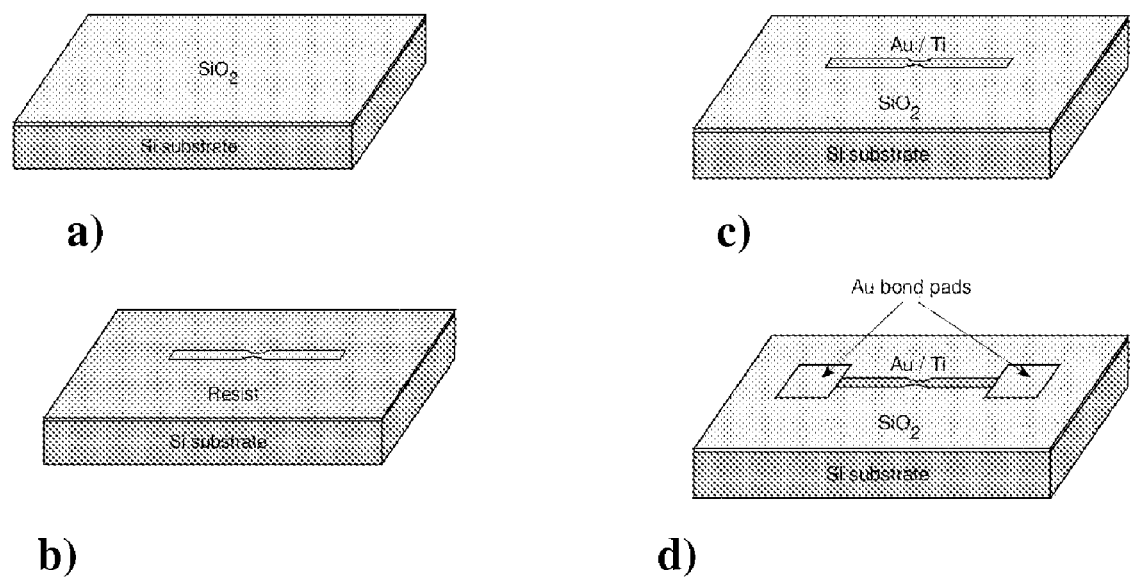

FIG. 19 depicts a Schematic diagram of process flow for an embodiment of device fabrication; a) 500 nm oxide on Si; b) Lithography (e-beam); c) Metallization (Au/Ti) & lift-off; d) Optical Patterning & deposition of bond pads.

Figure 20:
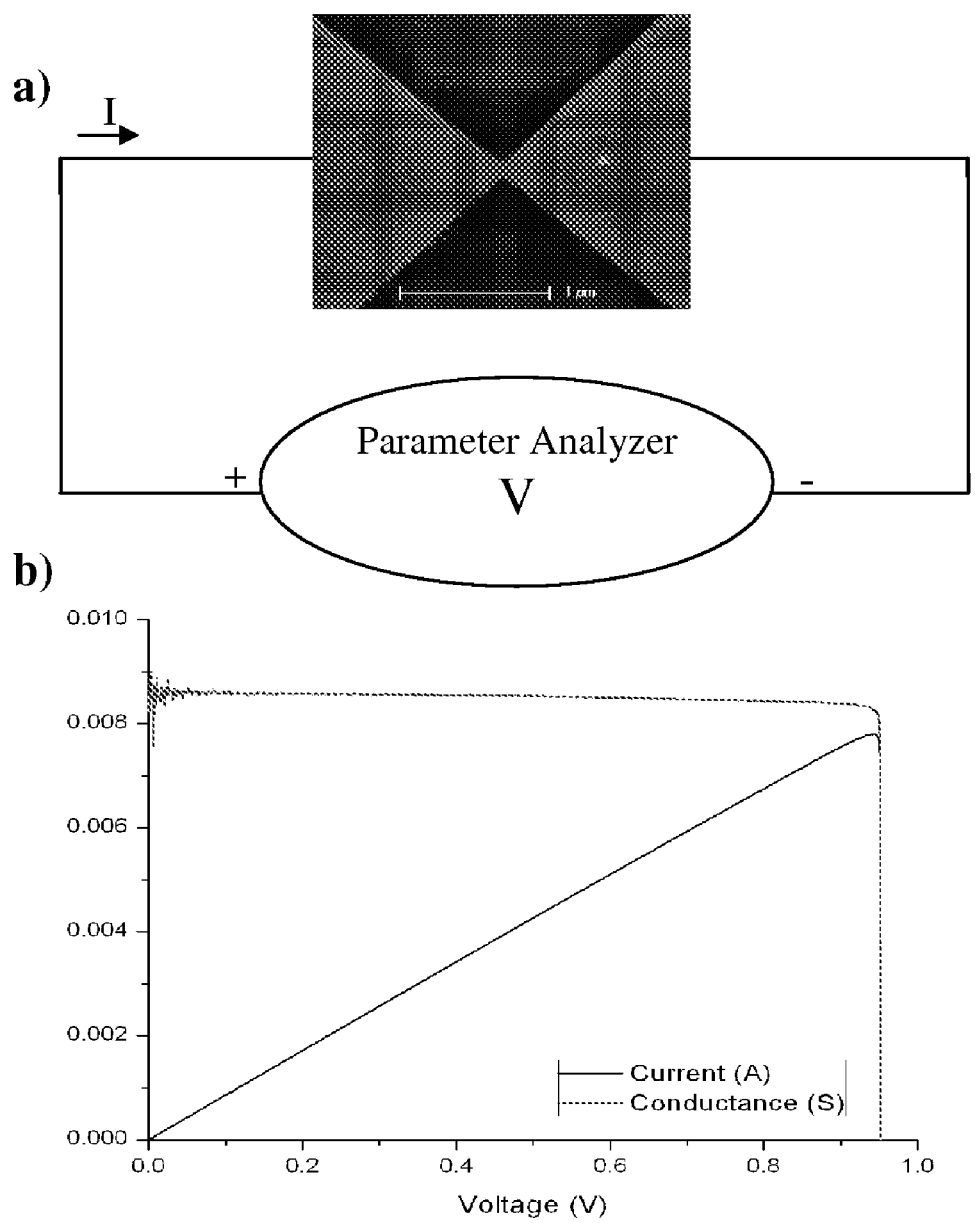

FIG. 20 depicts an embodiment for a) Circuit schematic; b) a typical IV curve as a function of V (time). 1V corresponds to 7000 s.

Figure 21:
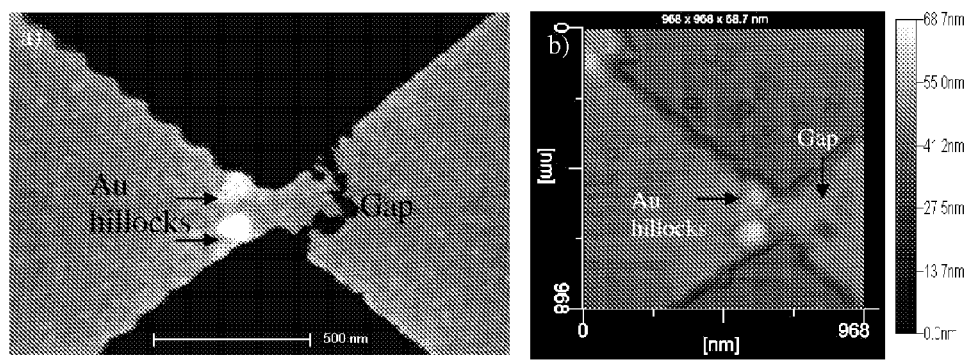

FIG. 21 demonstrates a) SEM image of a nanogap (left is anode side while right is cathode side); b) AFM topography of the nanogap. The bright spots in the SEM image and AFM images are gold hillocks.

Figure 22:
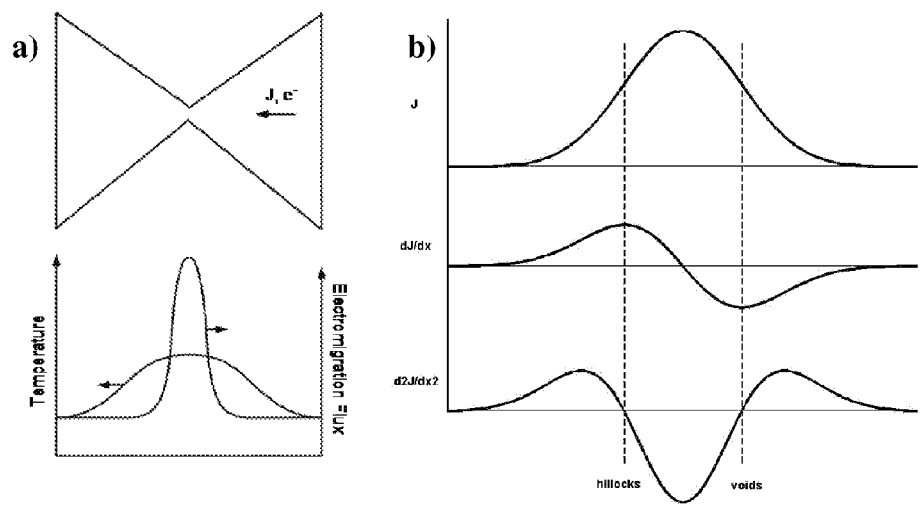

FIG. 22 depicts a) schematic drawing of temperature and electromigration flux; b) schematic drawing of current density J, dJ/dx and $d^2J/dx^2$.

Figure 23:
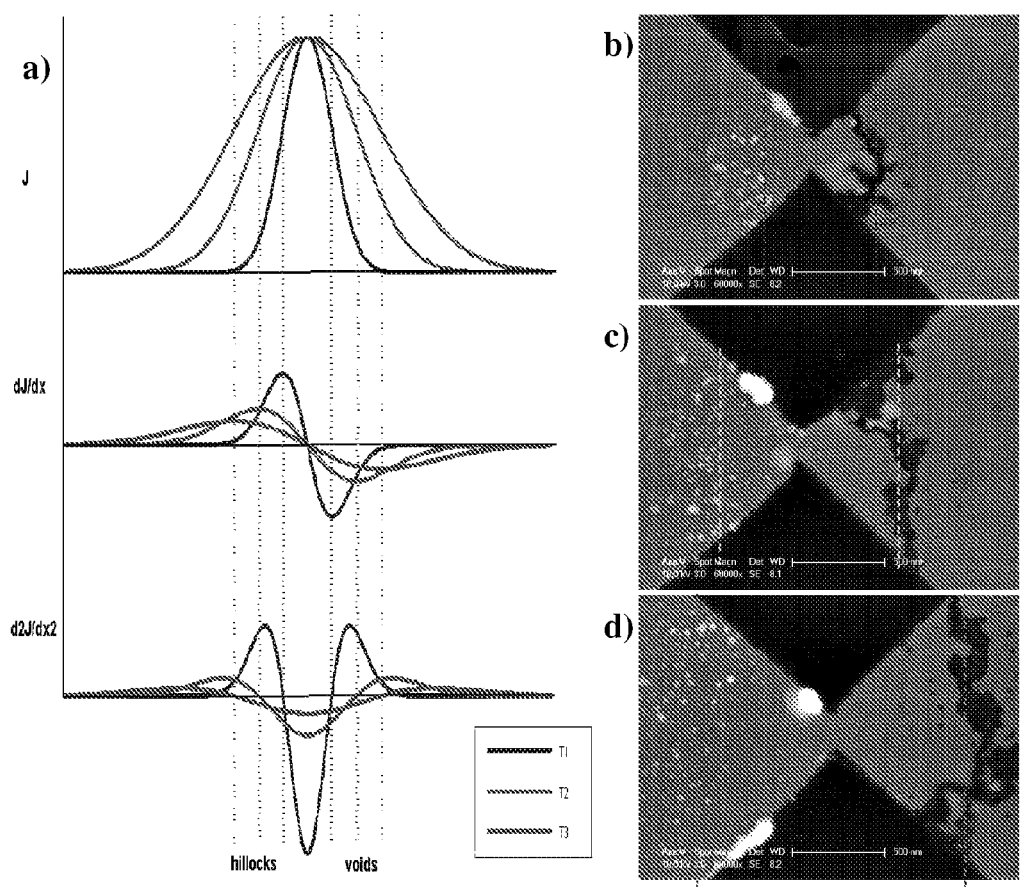

FIG. 23 depicts a) schematic drawing of J, dJ/dx and $d^2J/dx^2$ respect with various temperatures, T1<T2<T3; nanogap structures b) at room temperature; c) at 50° C.; d) at 90° C. The dot lines are positions of gold hillocks and gaps.

Figure 24:
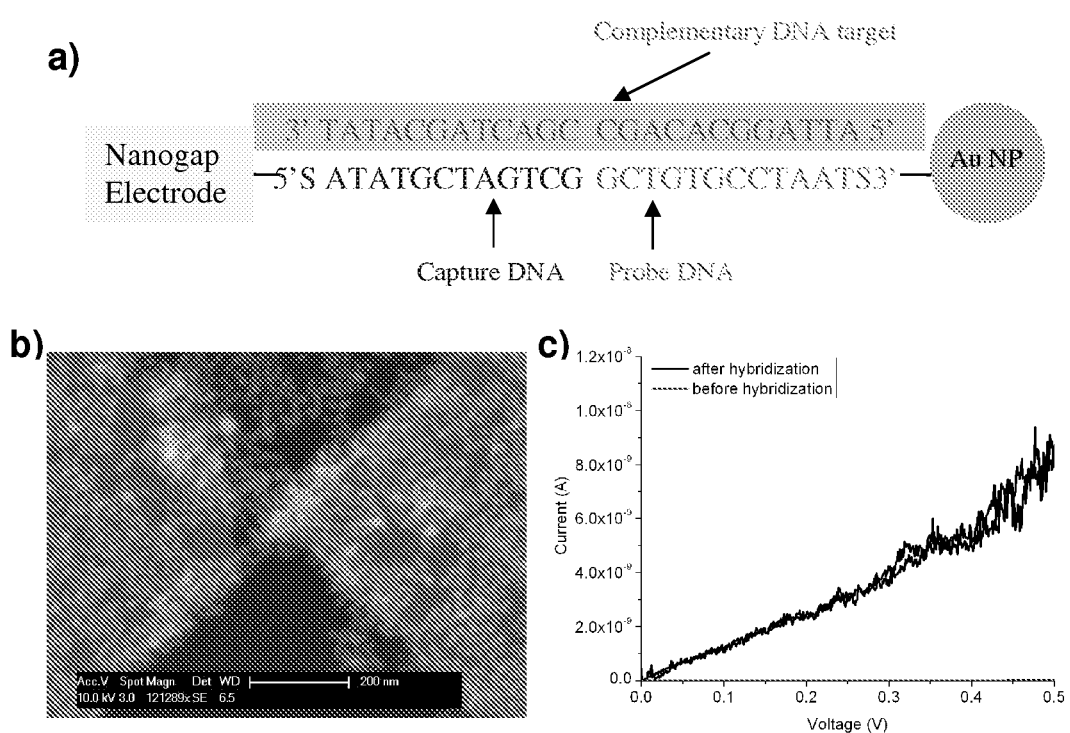

FIG. 24 depicts a) schematic of DNA hybridization detection; b) a SEM picture of a nanogap after DNA hybridization; c) IV characteristics of a nanogap before and after DNA hybridization.

DETAILED DESCRIPTION OF THE PRESENT INVENTION

This invention provides, in some embodiments, nanogap devices whose principal of operation relies on electrical conducting components of the device being covered by an insulating polymer layer, with the exception of a region proximal to the nanogap.

In some embodiments, any process to prepare such devices is considered to be a part of this invention. In one embodiment, the process comprises utilizing thermally-assisted electromigration of an electrode to form the nanogap whereby the heat generated by joule heating results in dissolution of a region of the insulating polymer layer proximal to the formed nanogap. Voltage sweeping may be used in this aspect, in some embodiments. In some embodiments selective dissolution of the insulating polymer may be accomplished, followed by feedback-controlled electromigration to form nanogaps. In some embodiments, such processes provide advantages such as simplicity of construction, or in some embodiments, reproducible means to control nanogap size in the devices of the invention.

In some embodiments, this invention provides for electrical detection of molecular properties while concurrently preventing interference by undesired ionic current flow through the device from the electrolytes in solution, and according to this aspect, such prevention is a function of the deposition of an insulating polymer on the majority of the exposed electrode surface. In some embodiments, the device relies on the detection of electric signals from nanogap alone, thereby increasing the signal-to-noise ratio in such nanogap detection devices and apparatuses.

Experimental results (FIG. 10) showed that the ionic current is reduced by two orders of magnitude when the nanogap device was protected by an insulation layer.

Nanogap Devices of the Invention

In one embodiment the invention provides a nanogap device for measuring changes in electrical properties or electrical responses of a sub-micron sized material, the device comprising:
  i. a substrate; and
  ii. at least one conducting electrode pair separated by a nanogap positioned on or within the substrate, wherein
     a first portion of the conducting electrode pair comprises an insulator coating; and
     a second portion of the conducting electrode pair proximal to said nanogap does not comprise an insulator coating.

In some embodiments, the nanogap is a nano-sized area separating between the ends of two electrodes. In one embodiment the nanogap area comprises air or gas. In one embodiment the air or gas are at a normal pressure and in other embodiments at reduced or elevated pressure. In one embodiment the nanogap is filled with a liquid. In one embodiment the nanogap is filled with solution. In one embodiment the nanogap is filled with aqueous solution and in other embodiments by an organic solution or an organic solvent.

In one embodiment the nanogap is geometrically defined by the substrate underneath it, and, in some embodiments, by the electrodes flanking it from at least two sides.

In some embodiments the nanogap geometry depends on the geometry of the ends of the electrode pairs flanking the gap. In one embodiment the geometry of the nanogap is rectangular or square. In one embodiment the geometry of the nanogap comprises curved edges. In one embodiment the curvature is positive and in other, the curvature is negative. In one embodiment the nanogap is formed directly on top of the substrate. In one embodiment the nanogap is suspended over the substrate. In one embodiment the nanogap width is uniform. In one embodiment, the nanogap width is non-uniform.

In one embodiment the width of the nanogap is defined by the distance between the electrodes. In one embodiment the height of the nanogap is defined by the height of the electrodes. In one embodiment the length of the nanogap is defined by the width of the end of the electrodes.

In one embodiment the width, height, length of the nanogap or a combination thereof ranges between 1 nm and 10 nm. In one embodiment the width, height, length of the nanogap or a combination thereof ranges between 0.1 nm and 1 nm. In one embodiment the width, height, length of the nanogap or a combination thereof ranges between 0.1 nm and 10 nm. In one embodiment the width, height, length of the nanogap or a combination thereof ranges between 10 nm and 100 nm. In one embodiment the width, height, length of the nanogap or a combination thereof ranges between 100 nm and 1000 nm. In one embodiment the width, height, length of the nanogap or a combination thereof ranges between 2 nm and 8 nm. In one embodiment the width, height, length of the nanogap or a combination thereof ranges between 10 nm and 75 nm. In one embodiment the width, height, length of the nanogap or a combination thereof ranges between 0.1 nm and 3 nm. In one embodiment the width, height, length of the nanogap or a combination thereof ranges between 0.1 nm and 5 nm. In one embodiment the width, height, length of the nanogap or a combination thereof ranges between 1 nm and 50 nm. In one embodiment the nanogap has a width ranging from between 0.5-100 nm. In one embodiment, the nanogap has a submicron width. In one embodiment, the width of the nanogap fits the dimensions of a sub-micron object. In one embodiment, a submicron object or a micron sized object spans the nanogap. In one embodiment, one region of an object can be in contact with one electrode, another region of the object can be in contact with a second electrode, and a third region of the object can reside in the nanogap or can be suspended over the nanogap. In one embodiment, the object can be in contact with the substrate underneath the gap, and in another embodiment, the object is not in contact with the substrate underneath the gap.

In one embodiment the nanogap is positioned between two electrodes. In one embodiment the nanogap is positioned between three electrodes. In one embodiment the nanogap is positioned between four electrodes. In one embodiment the nanogap is positioned between 2-100 electrodes.

In one embodiment, a device of this invention comprises a substrate, conducting electrodes, conducting contact pads for the electrodes, and complete or partial insulation for the various conducting components of the device.

In one embodiment the device has a height, length or width ranging between 1 µm and 10 µm. In one embodiment the device has a height, length or width ranging between 10 µm and 100 µm. In one embodiment the device has a height, length or width ranging between 100 µm and 1000 µm. In one embodiment the device has a height, length or width ranging between 1 mm and 10 mm. In one embodiment the device has a height, length or width ranging between 10 mm and 100 mm. In one embodiment the device has a height, length or width ranging between 5 mm and 15 mm. In one embodiment the device has a height, length or width ranging between 50 µm and 95 µm. In one embodiment the device has a height, length or width ranging between 110 µm and 190 µm. In one embodiment the device size ranges from between 100 nm to 10 cm.

In one embodiment the device is flat and in another embodiment the device is curved. In one embodiment the device is rigid and in another embodiment the device is flexible.

In one embodiment the device is constructed of materials, which can withstand high temperature. In one embodiment the device is compatible with low temperatures. In some embodiments the device is non transparent and in other embodiments the device is transparent.

In one embodiment the device is compatible for use with a liquid or a gas. In one embodiment the device materials is compatible with organic solvents. In one embodiment the device material can withstand high pressure. In one embodiment the device material is compatible with fluid or gas flow. In one embodiment the device is chemically and mechanically stable.

In one embodiment the device is comprised of a biocompatible material and is biocompatible.

In one embodiment, the term biocompatible refers to a low level of immune response to the material. In one embodiment, such material is termed biomaterial. In one embodiment, a biocompatible device can be implanted in a subject. In one embodiment, a biocompatible device is a device that will not cause the degradation or the decomposition of biological materials placed in the device unless specific operational modes are used.

For example and in one embodiment, biological materials can remain intact when placed in or on the device, and/or when a solution comprising biological material is flowing through the device, but once a biological material is trapped within a nanogap, electrical manipulation can cause changes in the biological material as described herein.

In one embodiment, horizontal and longitudinal axes of this invention are perpendicular to each other. In one embodiment, referring to a coordinate system, a horizontal axis may be parallel to an X axis, and a longitudinal axis may be parallel to a Y-axis. In one embodiment, the horizontal and longitudinal axes define a plane. In one embodiment, the plane defined by the X and Y axes is or is approximately the plane of the substrate.

The devices of this invention comprise a substrate on which or within which electrode pairs are positioned. In some embodiments, the term "substrate" is to be understood to comprise a single material or multiple layers of materials, with, in some embodiments, such layers imparting desired characteristics to the device, or to aid in its operation. In one embodiment, the term "substrate" refers to a surface, a support, a sealing material, a tray, a first layer, a base, a holder, a fixer, a carrier, a scaffold or a reinforcement for the device. In one embodiment, the substrate is flat or curved or is in the form of square, rectangle, circle, a pillar, a column or a cylinder. In one embodiment, the substrate provides backing material. In one embodiment, the substrate assists to sustain, contain and/or strengthen the device or components of the device.

In one embodiment the substrate in the devices of this invention is comprises of silicon. In one embodiment the substrate is comprised of silicon covered by a layer of silicon oxide or silicon nitride. In one embodiment the substrate is comprised of doped silicon. In one embodiment the doped silicon is conducting. In one embodiment the silicon is coated by aluminum. In one embodiment the aluminum coating is oxidized.

In one embodiment the substrate is comprised of a polymer. In one embodiment the polymer is PDMS.

In one embodiment, the substrate comprises any non-conductive material, or is coated with a non-conductive material. In one embodiment, the substrate comprises any ceramic or polymeric material.

In one embodiment, the substrate and/or other components of the device can be made from a wide variety of materials including, but not limited to, silicon, silicon dioxide, silicon nitride, glass and fused silica, gallium arsenide, indium phosphide, III-V materials, silicone rubber, aluminum, ceramics, polyimide, quartz, plastics, resins and polymers including polymethylmethacrylate (PMMA), acrylics, polyethylene, polyethylene terepthalate, polycarbonate, polystyrene and other styrene copolymers, polypropylene, polytetrafluoroethylene, superalloys, zircaloy, steel, gold, silver, copper, tungsten, molybdenum, tantalum, KOVAR, KEVLAR, KAPTON, MYLAR, teflon, brass, sapphire, other plastics, or other flexible plastics (polyimide), ceramics, etc., or a combination thereof. The substrate may be ground or processed flat. High quality glasses such as high melting borosilicate or fused silicas may be used, in some embodiments, for their UV transmission properties when any of the sample manipulation and/or detection steps require light based technologies. In addition, as outlined herein, portions of the internal and/or external surfaces of the device may be coated with a variety of coatings as needed, as will be appreciated by the skilled artisan.

In one embodiment the substrate is comprised of a membrane. In one embodiment the membrane is a silicon nitride membrane.

In one embodiment the substrate is comprised of a transparent material. In one embodiment the transparent material is glass, quartz or a polymer.

In one embodiment the substrate is rigid. In one embodiment the substrate is flexible. In one embodiment the substrate is flat. In one embodiment the substrate is curved. In one embodiment the substrate is folded to form a tube.

In one embodiment, substrate integrity is not compromised by corrosive materials or organic solvents. In one embodiment the substrate and the oxide layer of the substrate are stable such as silicon oxide on silicon.

In one embodiment, the device comprises at least one electrode pair. In some embodiments, the device comprises an array of electrode pairs, with each pair defined by their flanking of a nanogap, and the array being of any desired orientation or positioning within the device.

In one embodiment the electrode pair is electrically conducting. In one embodiment the electrode pair is comprised of gold. In one embodiment the electrode pair is comprised of silver, titanium, Pd, Pt, Au/Pd, Cu, Cr, Ag. In one embodiment the electrodes are comprised of carbon. In one embodiment the electrodes are comprised of a thin layer of chromium or titanium coated by a thicker layer of gold. In one embodiment such layering increases the adherence of the electrode to the substrate. In one embodiment, the electrodes comprise aluminum. In one embodiment, the electrodes comprise doped silicon.

In one embodiment the electrodes are arranged in butterfly geometry at regions proximal to the nanogap. In one embodiment, the butterfly geometry is depicted in FIGS. 1f and 2c. In one embodiment, butterfly geometry is a geometry wherein two triangles are joined at their vertexes or apexes.

In one embodiment the electrode pair comprises wires. In one embodiment the wire cross-section is spherical. In one embodiment the wire cross-section is oval, rectangular, square, triangular.

In one embodiment termini of the electrode differs in shape from the rest of the electrode. In one embodiment, electrode termini have a triangular shape. In one embodiment electrode termini are sharp, pointed, rounded, straight, wavy, or with a triangular or rectangular periodic shaped edge.

In one embodiment at least a portion of electrode width ranges between 10 nm-100 nm. In one embodiment at least a portion of the electrode width ranges between 50 nm-150 nm.

In one embodiment at least a portion of the electrode width ranges between 100 nm-1000 nm. In one embodiment at least a portion of the electrode width ranges between 100 nm-500 nm. In one embodiment at least a portion of the electrode width ranges between 1 nm-10 nm. In one embodiment the electrode width varies along the electrode. In one embodiment the electrode width is smaller in the proximity of the nanogap as compared with electrode width farther from the gap.

In one embodiment at least a portion of electrode height ranges between 10 nm-100 nm. In one embodiment at least a portion of the electrode height ranges between 50 nm-150 nm. In one embodiment at least a portion of the electrode height ranges between 100 nm-1000 nm. In one embodiment at least a portion of the electrode height ranges between 100 nm-500 nm. In one embodiment at least a portion of the electrode height ranges between 1 nm-10 nm. In one embodiment the electrode height varies along the electrode. In one embodiment the electrode height is less at a region proximal to the nanogap as compared with electrode height at a region distal to the gap.

In one embodiment at least a portion of electrode length ranges between 100 nm-1000 nm. In one embodiment at least a portion of the electrode length ranges between 500 nm-1500 nm. In one embodiment at least a portion of the electrode length ranges between 1 µm-10 µm. In one embodiment at least a portion of the electrode length ranges between 1 µm-5 µm. In one embodiment at least a portion of the electrode length ranges between 10 µm-100 µm. In one embodiment at least a portion of the electrode length ranges between 100 µm-1000 µm.

In one embodiment more than two electrodes surround the gap. In one embodiment, three or four electrodes surround the gap. In one embodiment the number of electrodes around the gap ranges between 1-100 electrodes.

In one embodiment the device comprises an array of electrode pairs. In one embodiment the array comprises 1-100 electrode pairs. In one embodiment the array comprises 100-1000 electrode pairs. In one embodiment the array comprises 1000-100000 electrode pairs. In some embodiments, arrays can be scaled up or down, as suitable for a particular application.

In one embodiment the electrodes are connected to contact pads via electrode termini at a region most distal to the nanogap. In one embodiment connection between the electrode pair and contact pads is achieved via evaporation of the gold comprising the contact pad in an area that overlaps with the area of the electrode end farthest from the nanogap.

In one embodiment, gate voltage can be applied through the substrate. According to this aspect and in one embodiment, the substrate comprises a conducting or a semi-conducting material covered by an insulator, and the conducting or semiconducting material is connected to a power supply. When voltage is applied to the substrate, it can affect the electrical properties of the nanogap, the vicinity of the nanogap and/or the electrical properties of an object placed within and/or on top of the nanogap. In one embodiment, applying such voltage assists in probing, detecting, measuring the properties of, measuring changes of and/or identifying an object in or on the nanogap, or the nanogap itself.

In one embodiment, insulating materials of this invention are electrically insulating, thermally insulating or both. In one embodiment, conducting materials of this invention are electrically conducting, thermally conducting or both.

In one embodiment, the device comprises an electrically insulating material. In one embodiment the insulating material is a polymer. In one embodiment the polymer is polymethyl methacrylate (PMMA). In one embodiment the polymer is poly acrylic acid. In one embodiment the polymer is polydimethylsiloxane (PDMS).

In one embodiment, the polymer comprises Bakelite, neoprene, nylon, PVC, polystyrene, polypropylene, polyethylene, polyacrylic acid, polyacrylonitrile, PVB, silicone or a combination thereof. In one embodiment, the polymer is natural and in another embodiment the polymer is synthetic. In one embodiment, the polymer is a bio-polymer. In one embodiment, the polymer is a co-polymer.

In one embodiment the height of the insulating material layer is 500 nm. In one embodiment the height of the insulated material layer ranges between 0.2 nm-20 nm. In one embodiment the height of the insulated material layer ranges between 50 nm-500 nm. In one embodiment the height of the insulated material layer ranges between 100 nm-1000 nm. In one embodiment the height of the insulated material layer ranges between 500 nm-2000 nm.

In one embodiment, portions of the electrodes are not coated by an insulating material, and such portions may have a size ranging from between 0.01% to 1% of the total electrode area. In one embodiment, portions of the electrodes are not coated by an insulating material, and such portions may have a size ranging from between 0.005% to 0.5% of the total electrode area. In one embodiment, portions of the electrodes are not coated by an insulating material, and such portions may have a size ranging from between 0.01% to 0.05% of the total electrode area. In one embodiment the portions of the electrode not coated by an insulating material have a size ranging between 0.001% and 0.01% of the total electrode area. In one embodiment, portions of the electrodes are not coated by an insulating material, and such portions may have a size ranging from between 0.001% to 0.005% of the total electrode area. In one embodiment the portions of the electrode not coated by an insulating material have a size ranging between 0.1% and 10% of the total electrode area. In one embodiment, the total electrode area comprises the contact pads area. In one embodiment, the total electrode area does not comprise the contact pads area. In one embodiment, electrode area is electrode surface area. In one embodiment, electrode area is the area that is not in contact with the substrate.

In one embodiment the device comprises a nanogap, which accommodates a sub-micron sized material.

In one embodiment, the sub-micron sized material is a biological or chemical molecule. In some embodiments the molecule is a peptide, a protein, a DNA, a lipid, a fatty acid. In one embodiment the sub-micron sized material is an aggregate of molecules. In one embodiment the aggregate is a vesicle, a micelle, a crystalline or an amorphous aggregate. In some embodiments the sub-micron sized material is a nanoparticle. In some embodiments the sub-micron sized material is a nanoparticle coated by molecules. In some embodiments the nanoparticle is a core-shell nanoparticle. In some embodiments the core is insulating or semiconducting and the shell is conducting. In some embodiments the shell is metallic.

In some embodiments the nanoparticle is transparent. In some embodiments the nanoparticle comprises indium tin oxide or tin oxide. In one embodiment the nanoparticle or a portion of the nanoparticle comprises gold, palladium, platinum, silver, copper, titanium, iron, nickel, aluminum chromium, or a combination thereof. In one embodiment the nanoparticle comprises GaAs, doped silicon, GaN, CdSe.

In some embodiments the geometry of the sub-micron sized material is spheric. In one embodiment the sub-micron sized material has a rod shape. In one embodiment the geometry of the sub-micron sized particle is a spiral, a tube, a cone, an oval, a wire, a square or a rectangular shape. In one embodiment more than one sub-micron sized object is present. In one embodiment 1-5 objects are present. In one embodiment 1-50 objects are present. In one embodiment, some objects are bonded to each other. In one embodiment a string of sub-micron sized objects bridge the nanogap. In one embodiment the objects are covalently bonded. In some embodiments the objects are held together by polar forces or by van-der-Waals forces.

In one embodiment the dimensions of the sub-micron sized object ranges between 1-1000 nm. In one embodiment the dimensions of the sub-micron sized object ranges between 0.3-1 nm. In one embodiment the dimensions of the sub-micron sized object ranges between 1-10 nm. In one embodiment the dimensions of the sub-micron sized object ranges between 10-100 nm. In one embodiment the dimensions of the sub-micron sized object ranges between 100-1000 nm. In one embodiment the dimensions of the sub-micron sized object ranges between 0.5-50 nm.

In some embodiments this invention provides an apparatus comprising the devices of this invention. In some embodiments, the apparatus comprises a power supply and/or a conductance measuring system operationally connected to the device. In some embodiments, the phrase "operationally connected" refers to the presence of elements such that the indicated parts are directly or indirectly connected and that the indicated parts are therefore capable of functioning properly. In some embodiments, the power supply is a DC power supply, or in some embodiments, an AC power supply. In some embodiments, the device operates on voltage applied at a range of 0V-10V. In some embodiments, the device operates on voltage applied at a range of 0V-1V.

In some embodiments, the apparatus further comprises a unit to induce fluid flow in said device. In some embodiments, the unit induces pressure-driven flow in the device, for example, syringe-driven or pump-driven application of the fluid to the device. In some embodiments, the unit induced electroosmotic flow, which conveys the fluid and thereby the material of interest to the nanogap in the device.

In some embodiments, the apparatus comprises any elements, which aid in the detection and/or quantification of changes in electrical properties or electrical responses or both, of a material placed in nanogaps of the devices of the invention.

In some embodiments, changes in the electrical responses or properties measured or calculated are conductance, inductance, resistance, capacitance or a combination thereof. In one embodiment the changes in electrical responses or properties detected or measured are changes in current, changes in resistance, changes in capacitance, conductance, voltage drop or a combination thereof.

In one embodiment the electrical response is measured in conjunction with or following the application of a voltage. In one embodiment the electrical response is measured in conjunction with the application of a magnetic field. In one embodiment the electrical response is measured in conjunction or in sequence with light irradiation.

In some embodiments the electrical response depends on the electrical properties of the contents of the nanogap. In some embodiments the electrical response is a function of the nature of the bonding between the electrodes and the object residing in the gap. In one embodiment the electrical response is a function of the number of objects residing in the gap. In one embodiment the electrical response is a function of temperature.

In one embodiment, the object is a nanotube, a fullerene, a nanoparticle, a quantum dot, a biological material, a protein, an enzyme, a DNA strand or sequence, a molecule, an atom, a cluster of atoms, a molecule, an aggregate of molecules, a polymer, a polymeric particle, a biological cell, a cell fragment, a virus, or a combination thereof. In one embodiment, the object can be organic, inorganic or a combination thereof. In one embodiment, the object can be electrically conducting, semiconducting or insulating. In one embodiment, the object can have a symmetric or an asymmetric geometry.

In one embodiment, the device is part of a larger microfluidic device. In one embodiment, a microfluidic device is a device wherein at least some of the components or elements have dimensions on the micrometer scale. In one embodiment, a microfluidic device comprises channel through which liquids or solutions can flow. In one embodiment, the channels have cross section on the order of micrometers. In one embodiment, devices of this invention can be placed in a microfluidic device such that the nanogap comprises the inner wall or an inner surface of a microchannel. In one embodiment, devices of this invention can be placed in a microfluidic device such that the nanogap comprises an inner surface of a reservoir. In one embodiment, fluid can flow on or over nanogaps when placed in a microfluidic device. In one embodiment, species of interest can be trapped in or on the nanogap from a solution or a fluid that is flowing over the nanogaps.

In one embodiment, unit to induce flow may be a unit that can induce pressure-driven flow and/or electro-osmotic flow. In one embodiment, flow can be based on capillary forces. In one embodiment, flow of some species is induced by diffusion of the species. In one embodiment, flow is induced by mixing or by applying a temperature gradient.

II. Processes to Prepare the Nanogap Devices of the Invention

In some embodiments, this invention provides for processes for preparation of the nanogap devices as described herein.

In one embodiment the invention provides a process for preparing a nanogap device, said process comprising: a. positioning a conducting material having a longitudinal axis, which exceeds its horizontal axis on a substrate, wherein said conducting material comprises a second portion having a thinner region along its longitudinal axis as compared to a first portion of the conducting material; b. applying an insulator coating to said conducting material; and c. applying a voltage to said conducting material; wherein application of voltage results in electromigration of atoms in the second portion forming a gap in the portion and heating of the second portion, resulting in at least partial removal of the insulator coating in the portion.

In one embodiment, the conducting material is a wire. In one embodiment the conducting material comprises two triangles connected at a point. In one embodiment such structure is referred to as a butterfly structure. In one embodiment, consecutive connected wires are leading to a central connected point wherein wires that are far from the central point have larger horizontal axis than wires closer to the central point. In one embodiment two cone structures are connected at their points.

In one embodiment the electromigration of atoms occurs after at least partial removal of the insulator coating.

In one embodiment the electromigration of atoms and said at least partial removal of the insulator coating are parallel processes.

In one embodiment the gap formed has a width ranging from between 0.5-100 nm.

In one embodiment the removal of insulator coating results in an uncoated area ranging between 0.01% to 1% of the total area of the conducting material.

In one embodiment the conducting material is comprised of gold, or any conducting material, as will be appreciated by the skilled artisan. In some embodiments, the conducting material may comprise any material as described for the electrode pair, as described herein.

In one embodiment the insulator coating is PolyMethylMethacrylate (PMMA), or any material as described herein or as known in the art.

In one embodiment the substrate is silicon, silicon dioxide or any material as described herein, or embodiment thereof, or as known in the art.

In one embodiment the process comprises preparation of a device comprising an array of electrode pairs.

In one embodiment the device is so constructed so as to be compatible for use with a liquid or a gas.

In one embodiment, when a hole is formed in the insulating layer on top of the thinner region of the electrodes before the nanogap is created, species of interest can be deposited or adhered to the electrodes before nanogap formation through the hole in the insulating material. In one embodiment, forming the nanogap after some species of interest are already bound to the electrodes, may better define nanogap dimensions. In one embodiment, having the species of interest bound or adhered to the electrodes before nanogap formation may increase the yield or improve the placement of the species of interest within or on top of the nanogap that will form.

In one embodiment, sub-micron is a term used to describe an object in which at least one dimension is smaller than one micrometer. In one embodiment a sub-micron object is an object in which at least one dimension ranges between 0.1 nanometer and 1000 nanometers.

In one embodiment, "proximal to a nanogap" means close to, in contact with, in close vicinity of, in loose or strong contact with, in and around, within, on top of, next to, over, suspended over, surrounding the nanogap or a combination thereof.

In one embodiment, a nanoparticle is a nanosphere. In one embodiment, a nanoparticle is a particle with at least one dimension ranging between 1 nanometers and 1000 nanometers.

In one embodiment the size and/or geometry of the device, or any other details regarding the device may comprise any embodiment as herein described.

In one embodiment the thin portion of the conducting material is suspended over the substrate. In one embodiment suspension is achieved by selectively etching a portion of the substrate underneath the thin portion of the conducting material. In one embodiment the etching is dry. In one embodiment etching is wet. In one embodiment, suspending the conducting material at the area of the gap will enhance the binding capability of the nanogap. In one embodiment suspension of a thin part of the conducting material enhances fluid flow around the conducting material.

In some embodiments, processes of preparation of the nanogap devices of this invention are as exemplified herein. It is to be understood that there are a number of ways to prepare nanogap devices as herein described, as will be readily appreciated by the skilled artisan and that such methods are to be considered as part of this invention.

In one embodiment the invention provides kits comprising the nanogap devices of this invention. In one embodiment the invention provides an apparatus comprising a nanogap device of the invention.

III. Methods of Use of the Nanogap Devices of the Invention

In one embodiment the nanogap devices of this invention may be used to measure an electronic property or electrical response of a sub-micron sized material.

In one embodiment the invention provides a process for measuring electrical properties or an electrical response of a sub-micron sized object, said process comprising:
a. placing a sub-micron sized material within a nanogap device, said device comprising:
  a substrate;
  at least one conducting electrode pair separated by a nanogap positioned on or within said substrate, wherein
    a first portion of said conducting electrode pair comprises an insulator coating; and
    a second portion of said conducting electrode pair proximal to said nanogap does not comprise an insulator coating; and
  a power supply operationally connected to said electrode pair;
  wherein said sub-micron sized object is within or proximal to said nanogap;
b. applying a voltage to said device; and
c. measuring an electrical response of said sub-micron sized object in said device.

In one embodiment the sub-micron sized material is a nanoparticle.

In one embodiment the sub-micron sized material is a drug, pollutant, toxin or biological material.

In one embodiment the submicron sized material is covalently bonded to said electrodes. The electrodes may comprise any embodiment as herein described, or as suitable, as would be appreciated by the skilled artisan (see for example, U.S. Pat. No. 5,156,810, fully incorporated herein by reference).

In one embodiment the electrical response is measured in solution.

In one embodiment the electrical response is measured as current, voltage, capacitance, inductance, conductance, resistance, or a combination thereof.

In one embodiment the invention provides a specific sensing of a molecule of interest, said method comprising:
a. placing a sub-micron sized material within a nanogap device comprising:
  a substrate; and
  at least one conducting electrode pair separated by a nanogap positioned on or within said substrate, wherein
    i. a first portion of said conducting electrode pair comprises an insulator coating; and
    ii. a second portion of said conducting electrode pair proximal to said nanogap does not comprise an insulator coating; and
  a power supply operationally connected to said electrode pair;
  wherein said sub-micron sized object is within or proximal to said nanogap;
b. applying a voltage to said device;
c. measuring an electrical response of said sub-micron sized material in said device, wherein said sub-micron sized material is proximal to said nanogap and wherein said sub-micron sized material comprises a targeting moiety;
d. introducing a fluid comprising a molecule of interest specifically interacting with, or suspected of specifically interacting with said targeting moiety, wherein specific interaction between said molecule of interest and said targeting moiety causes a change in the electrical response of said sub-micron sized material; and
e. detecting, measuring or a combination thereof said change in electrical response in (d);
whereby said change in electrical response serves as an indicator for specific sensing of the molecule of interest.

In one embodiment the targeting moiety is a protein, a DNA, an enzyme, a hapten, a lectin or a combination thereof.

In one embodiment, the term "targeting moiety" may refer to a fragment of the sub-micron sized material, which is the region of specific interaction with the molecule of interest. In some embodiments, the targeting moiety is a separate molecule from the sub-micron sized material, which is bonded thereto and specifically interacts with the molecule of interest.

In one embodiment the molecule of interest is a protein, a DNA, an enzyme, a hapten, a lectin or a combination thereof.

The targeting moiety and molecule of interest comprise cognate halves of a binding pair. Such cognate halves may be varied widely in size, for example being molecules of less than about 2 kD, less than about 1 kD, or greater than 10 kD, or any applicable size.

In some embodiments, either cognate half may be haptenic, which may include small organic molecules, including oligopeptides, oligonucleotides, saccharides or oligosaccharides, or the like. In some embodiments, either cognate half may be a macromolecule, in some embodiments not exceeding about 500 kDal, or in some embodiments not exceeding about 200 kDal. In some embodiments, either cognate half may comprise proteins, nucleic acids, or other polymeric or nonpolymeric compounds of high molecular weight. In some embodiments, either cognate half may comprise crown ethers which will bind to particular ions. In some embodiments, either cognate half may comprise macrocyclic complexes for the purpose of molecular recognition of various natural and non-natural compounds.

In some embodiments, the targeting moiety may comprise a moiety for covalent binding to another molecule. Carboxy groups may be activated with carbodiimide to react with alcohols, phenols and amines. Hydrazines may react with carboxylic acids, ketones and aldehydes, particularly under reducing conditions. Thiols can react with activated olefins, such as maleimide, acrylates, etc. or activated halides, e.g., α-chloroacetyl, and the like. For non-covalent or covalent binding, some enzyme substrates, inhibitors or suicide inhibitors may be employed with the complementary enzyme.

In many cases, particular ligands will be used for a variety of purposes. For example, biotin may be used to bind to avidin or streptavidin, where the complementary member may then be used to link a wide variety of other molecules. Various lectins may be employed to bind a variety of sugars which may be attached to molecules of interest. Specific ligands may be employed which bind to complementary receptors, such as surface membrane receptors, soluble receptors, or the like.

In some embodiments, either cognate half may comprise a receptor, such as an antibody, which includes IgA, IgD, IgE, IgG and IgM, which may be monoclonal or polyclonal. The antibodies could be intact, their sulfhydryl bridges totally or partially cleaved, fragmented to Fab2 or Fab, or the like. The intact and totally cleaved antibodies could be used to make a recombinant protein A-antibody hybrid, to be incorporated into the assay. Coupling through the antibody's oligosaccharide moiety to hydrazines can be achieved with the intact, partially and totally cleaved antibody. Maleimide linkages could be used for the intact, partially and totally cleaved antibodies, and the Fab2 fragment, while the Fab fragment could be incorporated in an antibody hybrid. The antibodies may be functionalized at the Fc portion to ensure the availability of the binding sites for further binding, yet be conjugated to the sub-micron sized material.

In some embodiments, various proteins which bind specifically to a complementary ligand may be employed, such as enzymes, lectins, toxins, soluble receptors, and the like. Illustrative proteins include DHFR, streptavidin, avidin, cholera toxin, lectins, the c-H-ras oncogene product, and nucleases. For linkages with oligosaccharides, hydrazine may used, by itself or bound to a polymer, e.g., poly(acrylhydrazide). Alternatively, biotin, nucleotides, or other molecular recognition analogs, or the like may be used. Nucleic acids, such as ssDNA or RNA may be employed. Maleimide linkages may be employed for linking to a thiol containing molecule, which may be biotin, avidin, any ligand or binding protein, sulfhydryl containing polymer, a nucleic acid, or molecular recognition analogs. For example, an intact antibody, with a functional oligosaccharide moiety, may be cleaved with periodic acid, and the resulting aldehyde reacted with the hydrazine under reductive conditions to form a stable carbon-nitrogen bond. For providing sulfhydryl groups to react with a maleimide, the antibody may be reduced at the hinge region, partially cleaved at the hinge region, or proteolytically cleaved near the hinge region for forming a thio ether with the activated olefin. In each case, care will be taken in selecting the method of linkage to ensure that the desired sites for binding to the complementary member of the specific binding pair are available for binding. Alternatively, sulfhydryl surfactants may be attached to sulfhydryl groups on the antibody molecules.

Methods for signal generation/biosensing will include direct and competitive antibody/antigen binding. Signals will be generated, for example, from antigen binding to biosensors, where the antibodies have been immobilized on the biosensor surface such that their antigen-binding sites are free for binding. Competition binding assays are used for small, usually monovalent analytes including proteins, peptides, oligosaccharides, oligonucleotides, drugs, and other small ligands. Competition assays involve the use of mono-or multivalent ligands for signal amplification.

In some embodiments, either cognate half may comprise biological receptors including those for hormones, neural transmitters other than the acetylcholine receptor (e.g., adrenergic, gamma aminobutyric, serotonergic, dopaminergic), vitamins and other nutrients, bacteria, viruses, serum lipoproteins and antibiotics. These other receptors, unlike a single antibody, can react with more than one substance. Thus, in addition to binding their "natural" ligands (i.e., those to which they are intended to bind or bind in living organisms), these other receptors can bind substances whose chemical or physical structure is similar to the chemical or physical structure of the natural ligands. Such "class" binding is the basis for drug activity and the toxicity of many substances. For example, the acetylcholine receptor (AChR) is normally present in animals and acts as a mediator of neural transmission. The acetylcholine receptor is bound in the membrane of nervous tissue cells and, upon interaction with acetylcholine (its natural ligand), changes conformation and initiates a series of membrane ionic charge changes, which, in turn, result in a nerve impulse.

At least two types of other substances can also bind to the acetylcholine receptor: substances which cause changes in the AChR and, ultimately, nerve stimulation and substances which block changes in the AChR conformation and, thus block nerve stimulation. For example, substances such as muscarine, phencyclidines, etc., can cause these conformational changes in the AChR and cause nerve stimulation. Substances such as nicotine, curare and the snake toxin alpha-bungarotoxin, can also bind to the AChR. These substances, however, block the ability of the AChR to change conformation and block nerve stimulation. As a result, an acetylcholine receptor-based biosensor of the present invention is useful to detect and quantify compounds or substances which act on the receptor. For example, such a biosensor is useful for the determination of organophosphorus compounds (e.g., diisopropylfluorophosphate, soman, sarin, VX) drugs (e.g., succinylcholine, nicotine, decamethonium, pilocarpine, carbachol, physostigmine), naturally-occurring toxins (including alpha bungarotoxin curare; atropine; homarine) and a variety of environmental chemicals and pollutants (e.g., malathion, diazinon, carbaryl). As a result, a sensor of this type can be used to determine such substances in, for example, situations in which chemicals or pesticides are made (e.g. manufacturing plants) or used (e.g., agricultural or farming uses, home gardening uses, defense applications), as well as in situations in which their presence and/or concentrations are monitored (e.g., water supplies, air concentrations). It also has medical applications (e.g., in a clinic, hospital, physicians practice) in determining drugs, viruses, hormones, toxins, etc. in patients.

In one embodiment, the electrical property or response will comprise determining changes in conductance, capacitance or inductance. Such devices and apparatuses for the determination of conductance, capacitance or inductance prior to and following the binding events described are well known to the skilled artisan, for example, using an LCR or impedance meter, a current meter, and others as will be appreciated by one skilled in the art.

In some embodiments, the measured change is in conductance, and detection is as described and exemplified herein. In some embodiments, according to this aspect, binding of the target molecule and cognate binding partner in the nanogap, result in conductance increases associated with an increase in the surface charge due to the additional charge of e.g. the binding partner, with such conductance increases serving as a readout or indicator for a binding event in this aspect of the invention. In some embodiments, the devices/methods/kits/principles described herein provide a significantly more reliable readout for a binding event for nanogap devices known to date, for use with aqueous solutions.

In one embodiment, detecting, measuring or a combination thereof of electrical response is used to qualitatively characterize said molecule of interest.

In one embodiment measuring of electrical response is used to quantitatively characterize said molecule of interest.

In one embodiment the fluid is an aqueous solution.

In one embodiment the device is comprised of a biocompatible material, which may be implanted within the body of a subject.

In one embodiment the molecule of interest is in the bloodstream of a subject, the fluid is the bloodstream of the subject and the device recirculates blood in the bloodstream.

Figure 11:
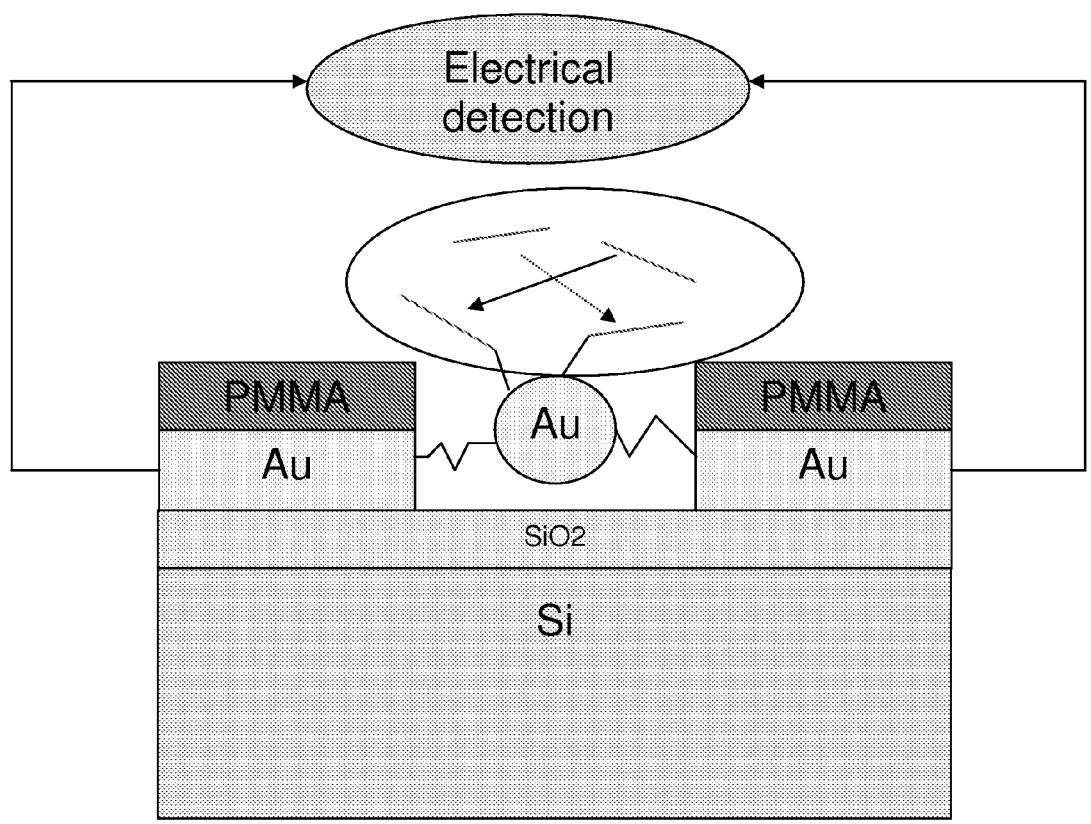
FIG. 11 schematically depicts use of an embodiment of a nanogap device of this invention as a biosensor.

In one embodiment, the devices/methods of this invention find application in biosensing. An example of a principle of operation of a biosensor based on the devices/methods of this invention is depicted in FIG. 11. Nanoparticles comprising a first molecule are placed in a nanogap, and upon interaction of the first molecule with a cognate second molecule, conductance changes occur, which may be detected, as depicted. In one embodiment, the gold electrode is functionalized using a dithiol group linker, enabling assembly of functionalized gold nanoparticles within the nanogap using dielectrophoresis (DEP).

In one embodiment the invention provides a process for electrically manipulating a sub-micron sized object, comprising:

a. placing a sub-micron sized material within a nanogap device comprising:
   a substrate; and
   at least one conducting electrode pair separated by a nanogap positioned on or within said substrate, wherein
      a first portion of said conducting electrode pair comprises an insulator coating; and a second portion of said conducting electrode pair proximal to said nanogap does not comprise an insulator coating, wherein said sub-micron sized material is proximal to said nanogap; and b. applying voltage to said device;

whereby application of said voltage results in a change in electronic configuration of said material, thereby electrically manipulating said material.

In one embodiment the change in electronic configuration induces a chemical change, a structural change, a conformational change, a binding event or a combination thereof in the sub-micron sized material.

In some embodiments, the terms "target molecule" and "sub-micron sized material" are interchangeable, and refer to any molecule with which another specifically interacts, wherein the interaction is of interest, and may be determined using the devices or methods or kits of this invention. In some embodiments, the term "cognate binding partner" refers to a second molecule, which specifically interacts with the target molecule. In some embodiments, the "target molecule" and "cognate binding partner" comprise a binding pair. In some embodiments, multiple target molecules have the same cognate binding partner, and in some embodiments, multiple cognate binding partners bind the same target molecule.

In one embodiment, the method is a screen to identify putative cognate binding partners for said target molecule. In one embodiment, the target molecule is a nucleic acid specifically hybridizing to a molecule comprising a sequence of interest, and said second liquid comprises nucleic acid molecules isolated from a biological sample.

In another embodiment the method is utilized to detect said species of interest when said species is present in said liquid at a concentration which is below a limit of detection.

In one embodiment, the method is a diagnostic method. In one embodiment, the method is used to identify biological or environmental toxins in a liquid sample.

In one embodiment, this invention provides an array architecture that is capable of being scaled to be suitable for a real-world screen.

By way of example, the devices/methods/kits of the present invention allow for high-throughput robotic assaying systems, to screen for a species of interest, or a binding partner of interest, and other applications, which may be applicable, inter alia, in screening promising drug candidates derived from libraries, for example, whose binding to a particular target molecule is of interest, or in some embodiments, in screening for the identification of molecular targets for drug design, for example screening for the identification of proteins, which interact with viral or bacterial cytotoxins, and others as will be appreciated by the skilled artisan.

In one embodiment the submicron sized material is a nanoparticle.

In one embodiment the sub-micron sized material is a drug, pollutant, toxin or biological material.

In one embodiment the process is conducted in solution.

In one embodiment the solution is aqueous.

In one embodiment the solution comprises a binding moiety, a reporter or indicator compound.

In one embodiment the changes in electronic configuration of said sub-micron sized material results in an ability to detect or quantify said reporter or indicator compound.

In one embodiment the indicator compound is an ion or a fluorescent molecule, a photochromic compound, a halochromic compound, an ionochromic compound, a thermochromic compound or an electrochromic compound.

In one embodiment the changes in electronic configuration alter the binding properties of said sub-micron sized material.

In one embodiment altering said binding properties result in binding to a ligand.

In one embodiment the ligand is an enzyme, protein or an antibody.

In one embodiment the binding moiety binds said sub-micron sized object as a result of said change in electronic configuration of said sub-micron sized object.

In one embodiment the binding moiety is an ion, a molecule, a nanoparticle or a combination thereof.

In one embodiment the molecule is a DNA, a protein, a fluorescent marker or a combination thereof.

In one embodiment the protein is an enzyme.

In some embodiments, the particles comprise a material which allows for localized selective surface modifications such that binding of a molecule of interest is specific. Such functionalized beads are known in the art and readily available from commercial vendors, as will be appreciated by one skilled in the art.

In some embodiments, the devices and methods of use thereof of the invention provide the advantage of eliminating undesirable parallel conductive paths of nanogap devices when performing aqueous sensing. The magnitude of ionic current has been reduced by orders of two. In some embodiments, the processes of this invention allow for the preparation of nanogap devices via a method that is self-aligned so as to avoid fabrication complexity.

In one embodiment, this invention provides a self-aligned process to fabricate selectively insulated nanogap devices for biosensing application. In one embodiment, a thin PMMA layer is spun on fabricated gold electrode with a constriction. In one embodiment, when applying a slow voltage sweep until the electrode breaks down, there is simultaneous hole formation in PMMA layer and nanogap formation in gold electrode. This self-aligned process provides selectively insulated nanogap devices, which according to this embodiment, significantly reduce ionic conduction from electrolyte in e.g. biosensing. In one embodiment, the mechanism of the hole formation in the PMMA layer is heat induced evaporation. In one embodiment, this proposed mechanism has been proven by in situ AFM and laser annealing simulation.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

EXAMPLES

Example 1

Fabrication of Nanogap Devices

In one embodiment of the present invention, a nanogap device is fabricated such that all electrical conducting parts in the nanogap device were covered by an insulating polymer layer except in the vicinity of the gap.

Two techniques were developed to accomplish this design. Thermally assisted electromigration of atoms was used to form a nanogap in a conducting wire and heat generated by joule heating formed a hole in the insulating polymer layer at the position of the nanogap at the same time, using voltage sweep. The technique provides the advantage of great simplicity and versatility, in some embodiments.

The second technique involved a two step method, where a insulator-coated conducting was utilized and a hole was created in the insulating layer to form the nanogap using selective dissolution of the insulating polymer. This step was followed by feedback-controlled electromigration to form a nanogap. The technique provides an advantage, in some embodiments, in terms of the ability to control nanogap size and reproducibility in terms of obtaining the desired device.

Figure 1:
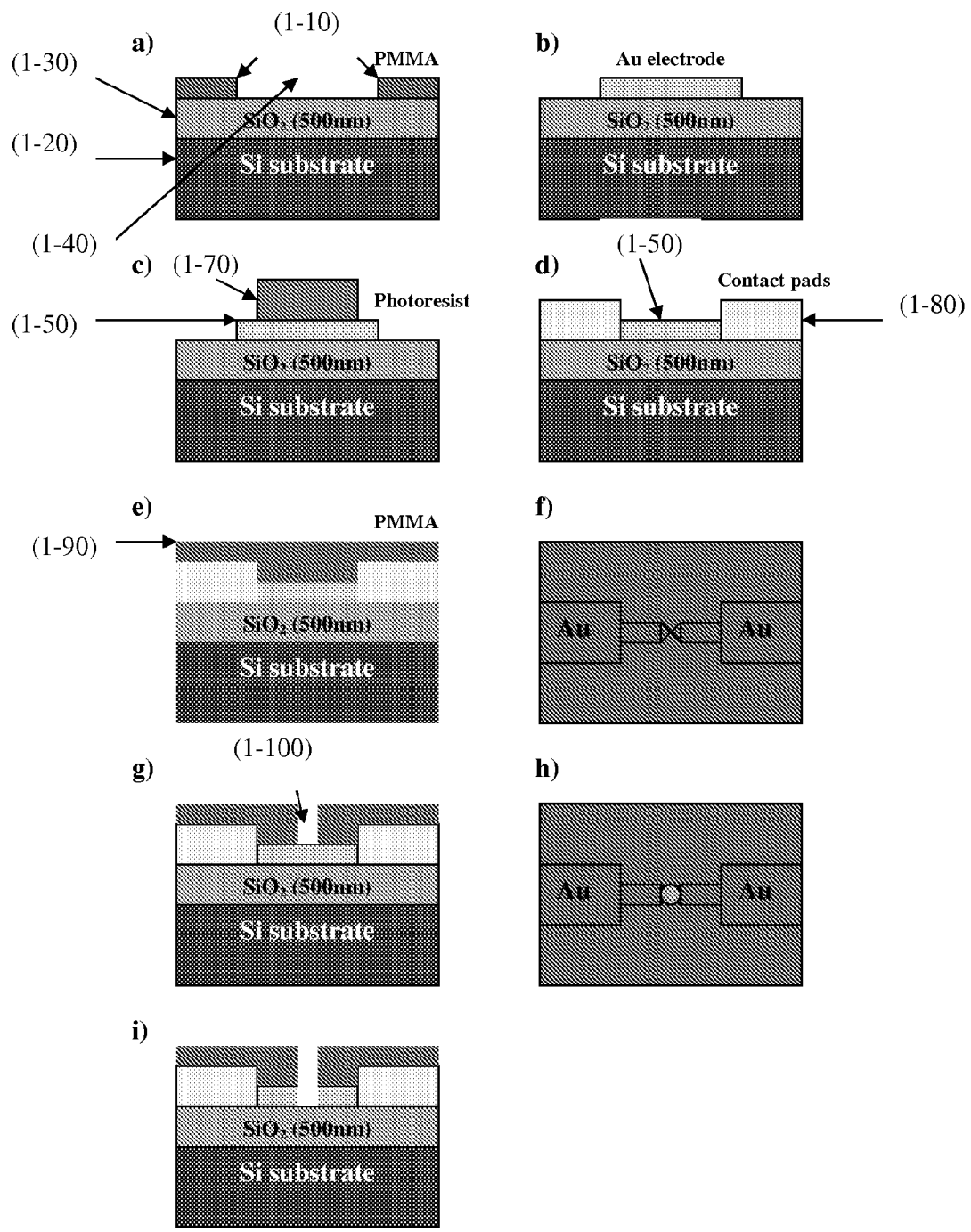
FIG. 1 depicts a schematic of an embodiment of a process of device fabrication: a) PMMA (1-10) is spun on a silicon substrate (1-20) covered by a layer of insulating silicon dioxide (1-30). Selected areas in the PMMA layer interacts with an electron beam (not shown), and are removed using a solvent. A gap (1-40) is formed in the PMMA layer; b) a gold electrode (1-50) is patterned on the substrate in (a) by gold evaporation into the gap in the PMMA layer. Removal (lift off) of the remaining PMMA is conducted using an organic solvent.; c) optical lithography using an additional layer of photoresist (1-70) is carried on in order to construct the contact pads; d) a gold electrode (1-50) and contact pads (1-80) after evaporation and lift-off; e) insulating layer (1-90) spun on the whole device; f) top view of e); g) an insulating-layer protected electrode after removing the insulating layer in the proximity of the future nanogap; h) top view of g); i) an insulating layer protected nanogap device after forming a gap (1-100) in the gold structure using electromigration.

FIG. 1 depicts a schematic of an embodiment of a process of device fabrication. A die was patterned in order to define the electrode with a weak junction, called butterfly structure, by electron beam lithography using polymethylmethacrylate (PMMA) (1-10) resist (FIG. 1a) on a silicon substrate (1-20) covered by a layer of insulating silicon dioxide (1-30), selected areas in the PMMA layer interacts with an electron beam (not shown), and are removed using a solvent and a gap (1-40) is formed in the PMMA layer. A metal layer of 16 nm-thick gold and 1.5 nm-thick Cr (as adhesion layer) was thermally evaporated (BOC Edwards, Auto 306 Vacuum Evaporator) to the resist-patterned die and lifted-off in acetone, to define the gold electrode (FIG. 1b) (1-50). This was followed by optical lithography using AZ5212 photoresist (1-70) to define large contact pads (400 um×400 um) (FIG. 1c). A second layer of 150 nm-thick gold and 15 nm Cr was thermally evaporated and lifted-off to deposit the contact pads (FIG. 1d) (1-80). An insulating polymer layer (1-90), in this case PMMA was used, was spun to cover the whole device (FIG. 1e, 1f). Next, the die is bonded on a 24-pin Standard IC package and ready for self-aligned nanogap and insulating hole formation (1-100).

Figure 2:
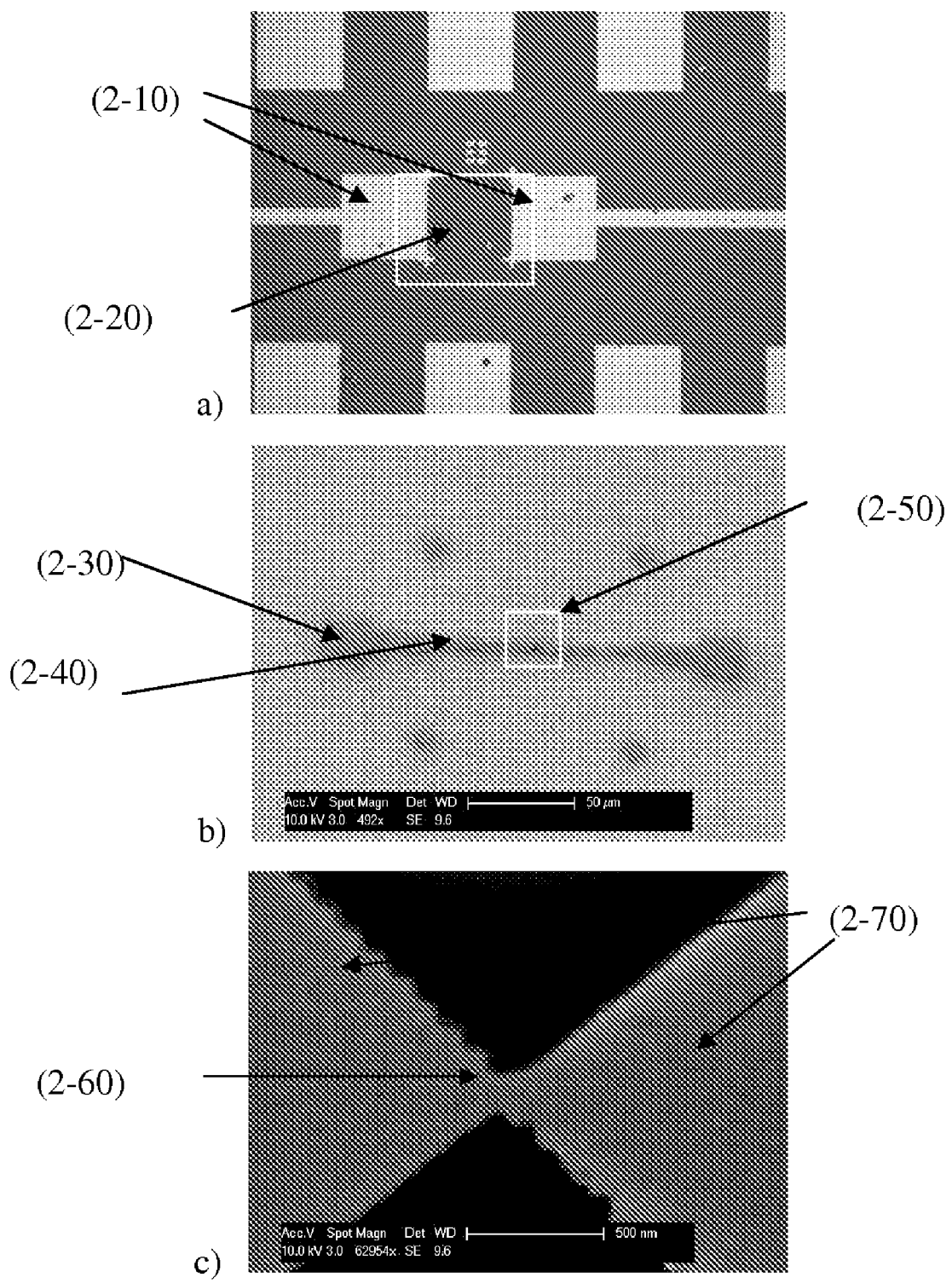
FIG. 2(a) is an optical micrograph demonstrating an embodiment of a device of this invention. Gold contact pads (2-10) are attached to the conducting wire/future electrode pair (2-20); b) is an SEM micrograph depicting the contact pads (2-30), the conducting wire (2-40) and a window around the central nanogap area (2-50); c) is a higher magnification SEM micrograph of the central gap area (2-60), showing the butterfly gold structure (2-70) wherein the gap will be formed.

FIG. 2 demonstrates an embodiment of a device prepared by a method described hereinabove. According to this aspect, Gold contact pads (2-10) were attached to the electrode pair (2-20) flanking the central nanogap area (2-50). At higher magnification the butterfly gold structure (2-70) was evident.

Figure 3:
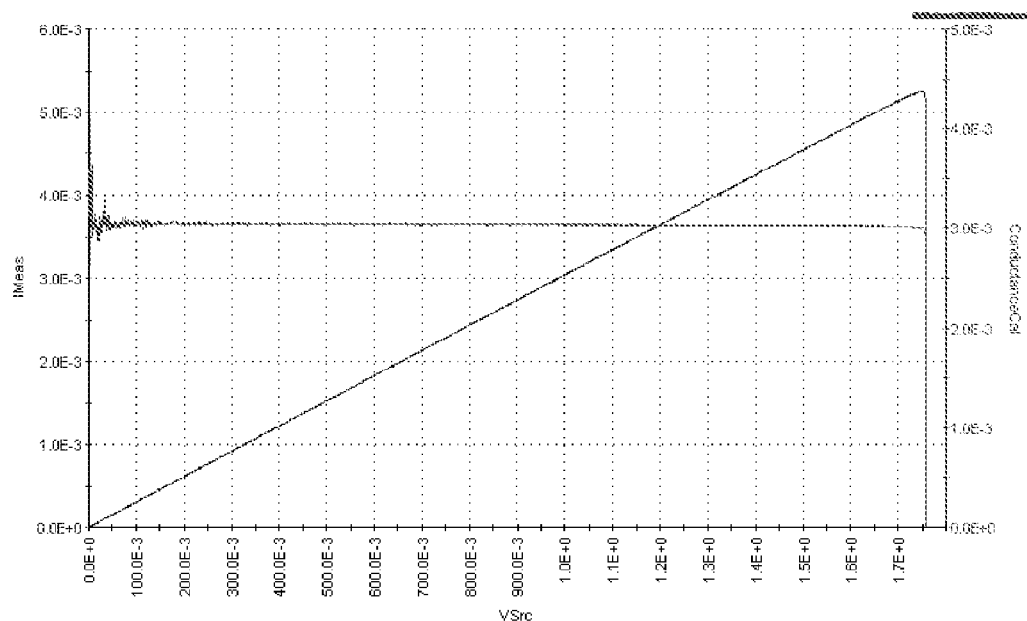
FIG. 3 depicts an IV curve of voltage sweeping showing the electromigration process. The x-axis represents the applied voltage in units of volts. The Y axis (left) represents the measured current in units of Ampere. The Y axis (right) represents the calculated conductance in units of Siemens. The figure shows the voltage ramp up to the point where a gap is formed in the conducting wire. The gap is formed when the voltage reaches about 1.8V. The gap forming voltage is indicated by the dramatic reduction in current due to the insulating properties of the gap.

When voltage was applied to the electrode, per one aspect of the fabrication method described herein, the voltage application having a step of 1 mV with a 3 seconds delay, the current density at the weak junction was highest for the smallest cross section area. Hence, electromigration of gold atoms there occurred as responding to the momentum carrying electrons. At the same time, the heat generated by joule heating ($P=I^2R$) enabled insulating polymer reflow and eventually formed a hole at the nanogap (FIG. 1i). FIG. 3 demonstrates an IV curve of voltage sweeping applied to the gold electrode, in one embodiment of a device of the invention as described herein. When the gap formed the voltage reached about 1.8V. The gap forming voltage was indicated by the dramatic reduction in current due to the insulating properties of the gap.

Figure 4:
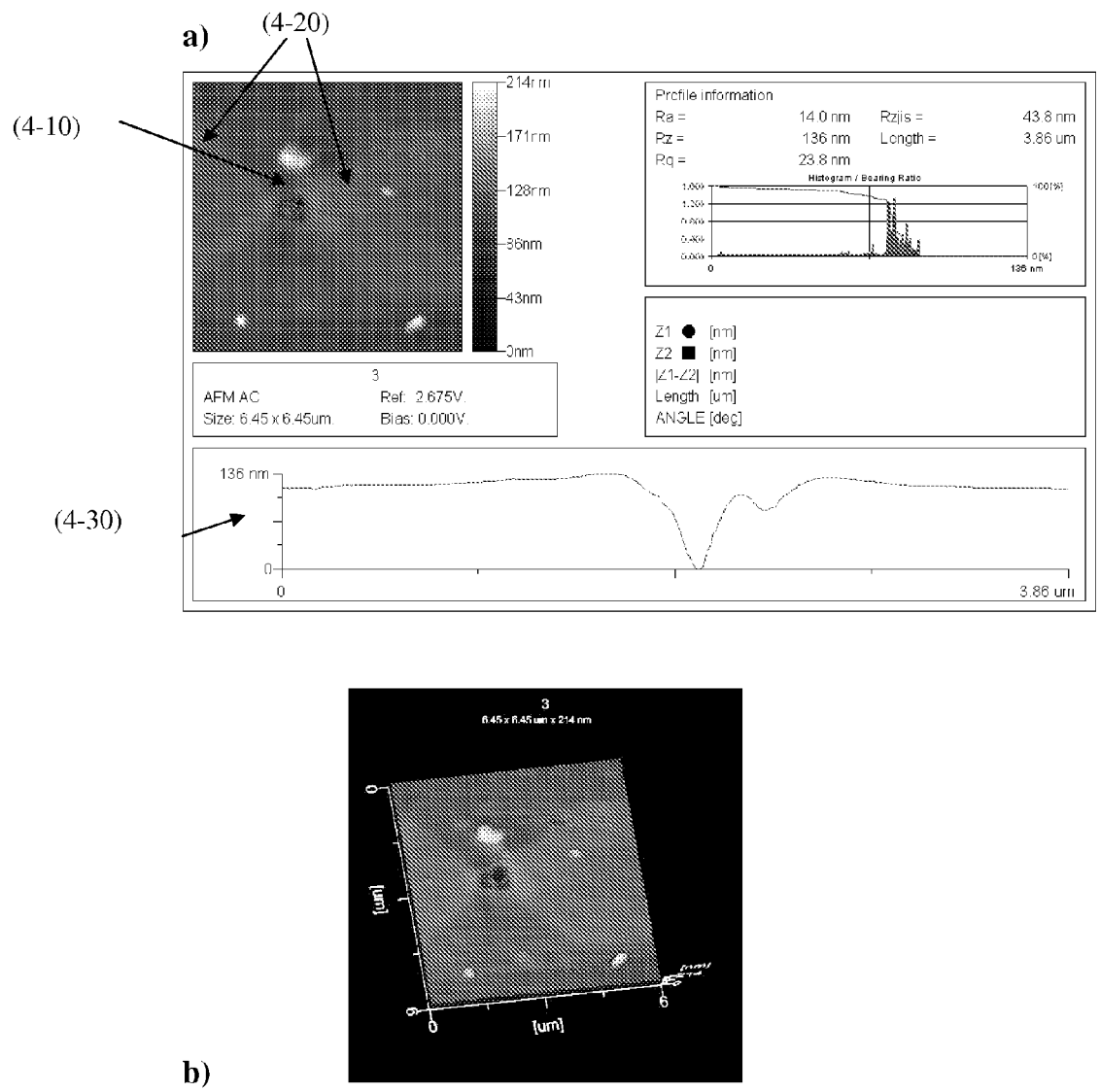
FIG. 4 demonstrates the results of an AFM experiment. (a) topography of an insulating layer protected nanogap (4-10) with a butterfly gold structure leading to the gap (4-20), and a line profile showing the reduction in height where the insulating layer was removed(4-30). (b) depicts a 3D display of (a).

AFM was conducted (FIG. 4), as well, and the topography of an insulating layer protected nanogap (4-10) with a butterfly gold structure leading to the gap (4-20), and a line profile showing the reduction in height where the insulating layer was removed (4-30) was evident. A three-dimensional display was obtained.

Figure 5:
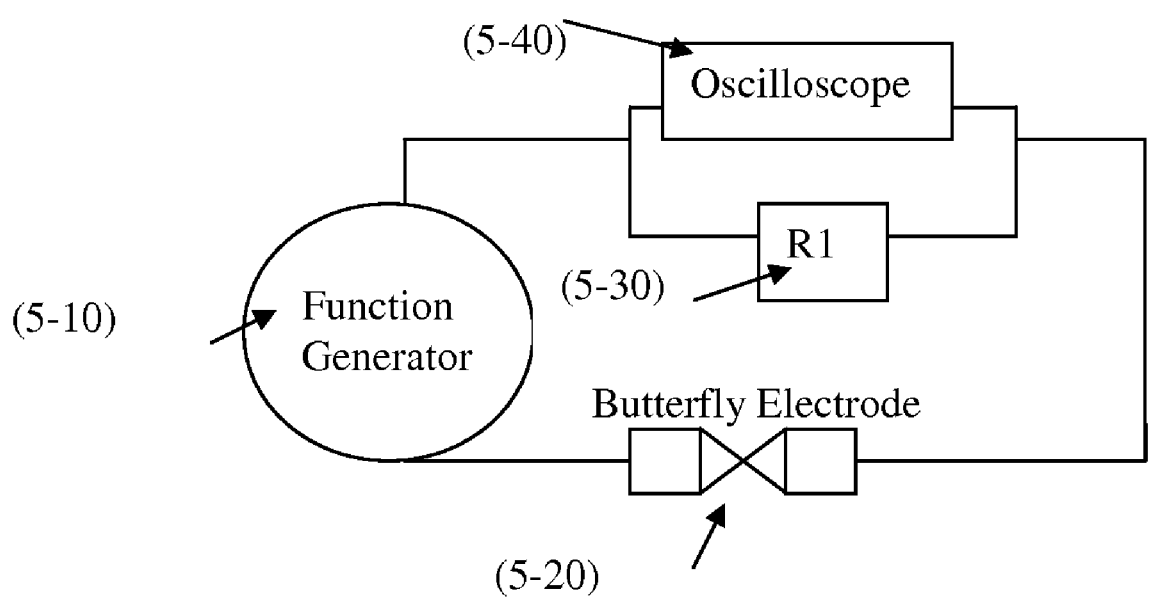
FIG. 5 schematically depicts a circuit design used for the removal of the polymer at the thinner part of the conducting wire, and for breaking the wire through electromigration. The function generator (5-10) is used to apply a voltage to the butterfly-shaped area of the conducting wire (5-20). The resistor R1 (5-30) controls the amplitude of the current generated. The oscilloscope (5-40) is used to measure voltage as a function of time.

A circuit design can be envisioned, which would be useful in the preparation of devices of this invention, for example by the methods described herein (FIG. 5). The function generator (5-10) applies a voltage to the butterfly-shaped area of the conducting wire (5-20). The resistor R1 (5-30) controls the amplitude of the current generated. The oscilloscope (5-40) is used to measure voltage as a function of time.

Figure 6:
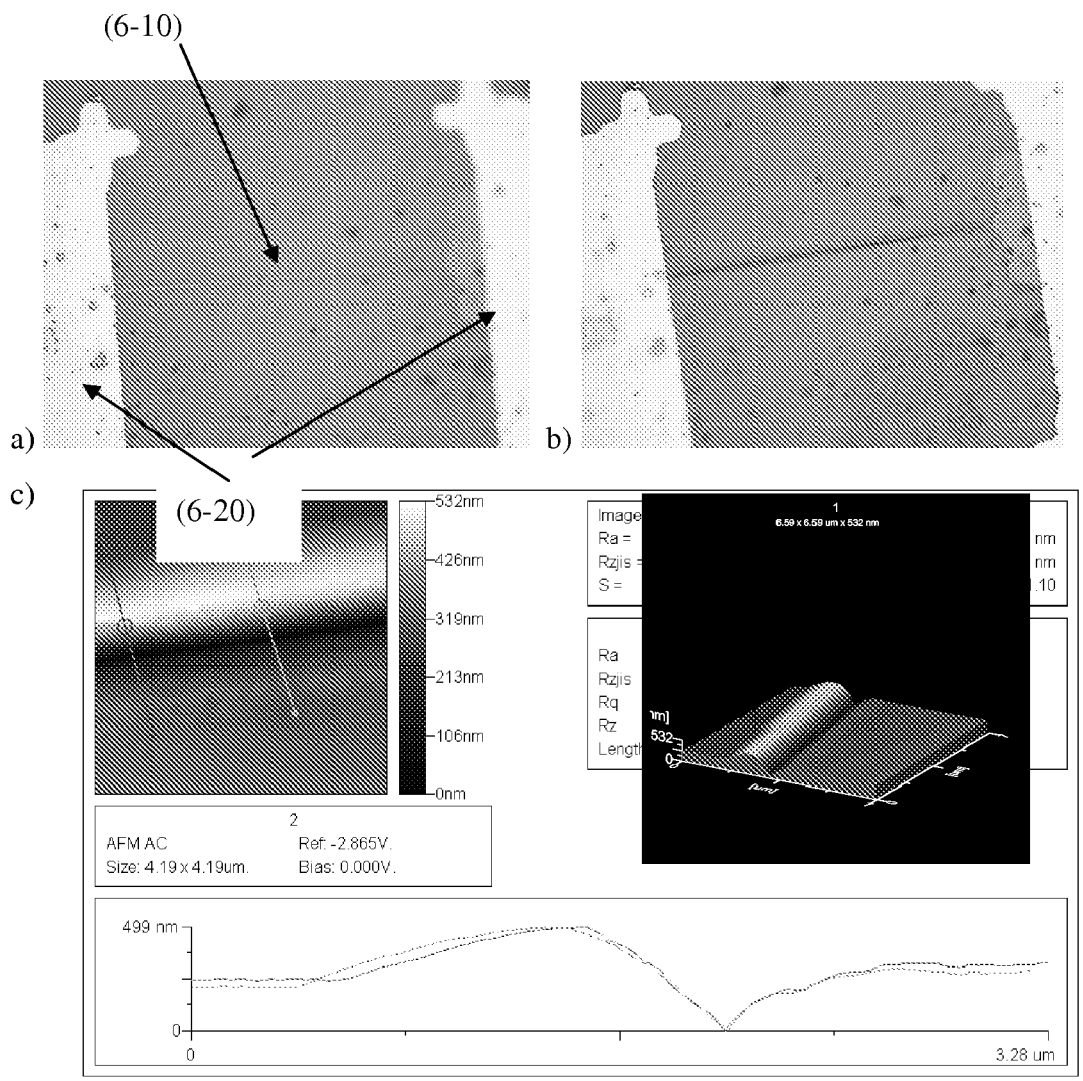
FIG. 6 is a micrograph of an embodiment of a device prepared by a process of the present invention. The conducting wire (6-10) and the contact pads (6-20) are shown (a) before and (b) after selective dissolution of the insulating polymer. (c) an AFM topographical picture showing a conducting wire positioned on an $Si/SiO_2$ substrate.

In one embodiment of a device prepared by a process of the present invention (FIG. 6), the conducting wire (6-10) is subjected to selective dissolution of the insulating polymer.

Figure 7:
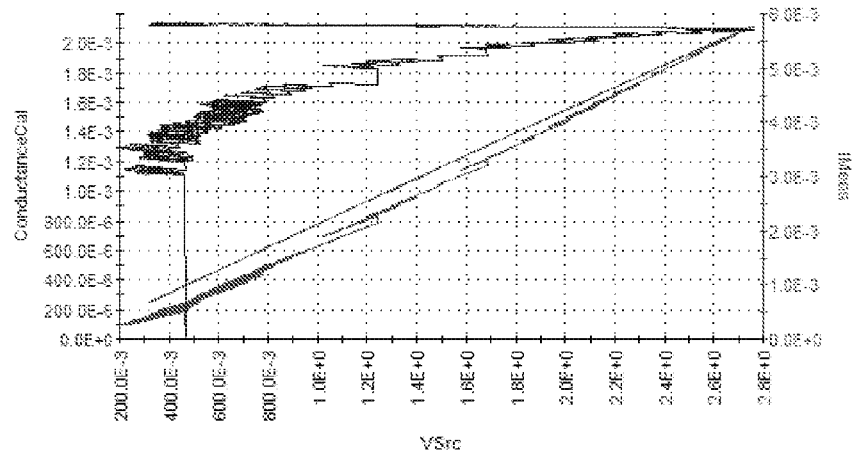
FIG. 7 plots current and conductance as a function of voltage for a feedback controlled electromigration process. A typical IV curve is shown.

Feedback-controlled electromigration may also be used as part of the processes of this invention to form nanogaps (FIG. 1i). A program may be integrated with a semiconductor parameter analyzer to carry out feedback-controlled electromigration. In one embodiment of a device of this invention prepared by a process according to this aspect, the conductance of the electrode was monitored. A reference conductance value at a voltage of 400 mV was measured and recorded. Then the voltage was swept up at 4 mV/s until the conductance dropped by a set fraction of the reference conductance value. At this point of time, the voltage was ramped down by 200 mV and then swept up again so that voltage applied was around the critical point for electromigration to avoid thermal breakdown of the structure (FIG. 7).

Figure 8:
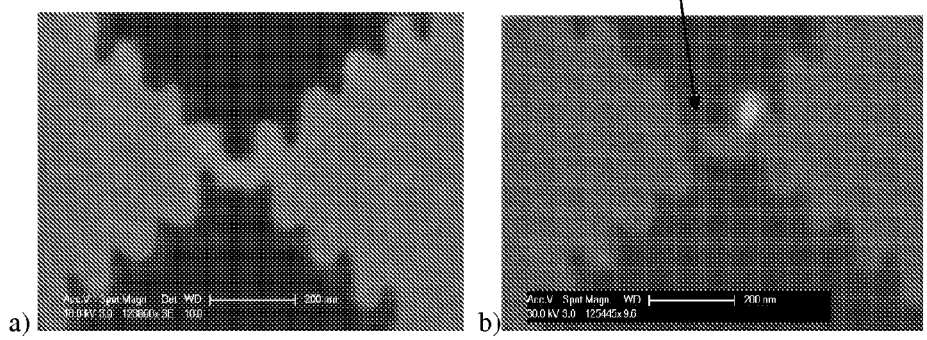
FIG. 8 depicts SEM micrographs of (a) a butterfly electrode before the formation of the nanogap; and (b) a nanogap (8-10) formed by feedback-controlled electromigration. The nanogap size is about 10 nm.

An embodiment of such a device is shown in FIG. 8, where a nanogap was formed from a butterfly electrode by feedback-controlled electromigration. The nanogap size is about 10 nm.

Figure 9:
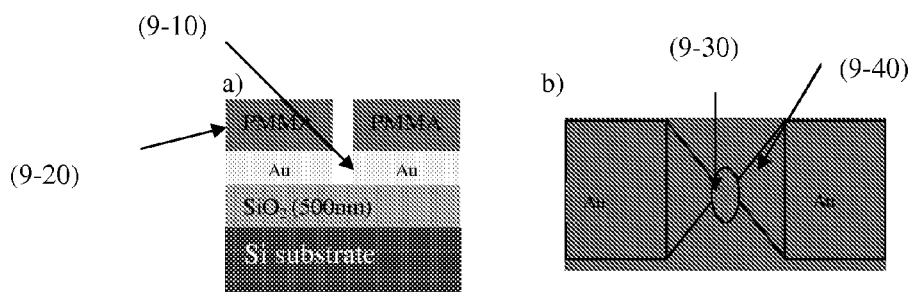
FIG. 9 is a schematic of an embodiment of a device of this invention showing an insulating layer protected nanogap. The area of the nanogap (9-10) corresponds to the area in which the insulating polymer layer (9-20) was removed. A (a) cross-sectional view and (b) top view of the nanogap area (9-30), in the central part of the butterfly gold structure (9-40) is shown.

In another embodiment of the preparation of a device of this invention (FIG. 9) the nanogap (9-10) corresponds to the area in which the insulating polymer layer (9-20) was removed.

Figure 10:
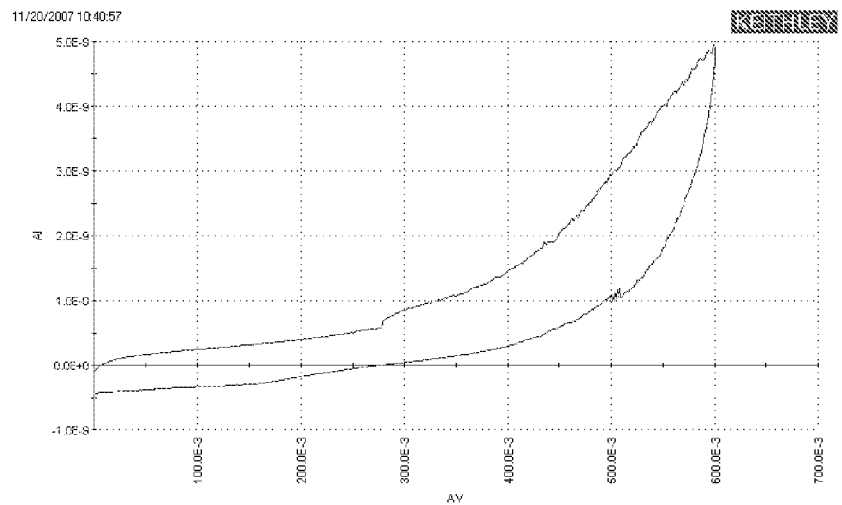
FIG. 10 plots current (Ampere) measured versus voltage (Volts) applied for two nanogap devices. (a) I/V curve for a nanogap without an insulating layer. (b) the I/V curve for a nanogap with an insulating layer everywhere except for the nanogap area. The experiment was conducted in an ionic liquid solution of 0.1M $CaCl_2$. The current in the insulated device is lower by two orders of magnitude when compared with the current in the non-insulated device.
Figure 10:
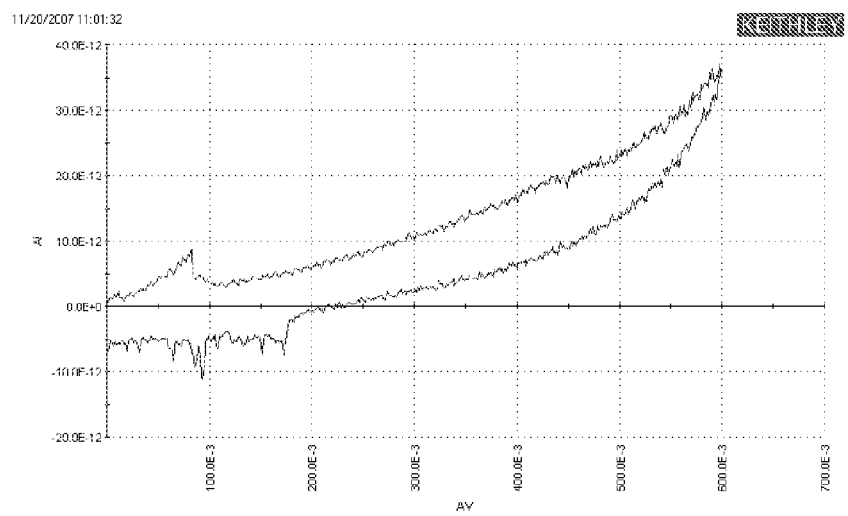

Devices prepared by either of these processes blocked undesired ionic current from electrolyte at areas insulated by the polymer, such that signal arising from the nanogap was distinct (FIG. 10). Experimental results showed that the ionic current was reduced by two orders of magnitude when the nanogap devices were insulated as compared with the non insulated nanogap devices (FIG. 10). Accordingly, the devices allowed for an increase in the signal-to-noise ratio of an electrical measurement conducted using the device.

Example 2

Probing the Electronic Properties of a Single Molecule

The nanogap devices of the present invention are used to probe the electrical properties of a single molecule or of small aggregates of molecules. A single molecule can be incorporated in the gap during or after the electromigration process. A molecule can be introduced to the gap from a solution of molecules surrounding the gap. An alternate method to incorporate a molecule in the gap is to coat the conducting wire with molecules, prior to coating the wire with the insulating material. When the gap is formed, molecules adjacent to the gap, can fall into the gap or become suspended over the gap. In some embodiments, molecules can bridge the gap, by binding to the two newly-formed electrodes. According to this aspect, and in some embodiments, molecules can comprise one or two functional end groups that adhere to the electrode material. In some embodiments, trapping of molecules in the gap can be accomplished via self-assembly of molecules from solution, or in some embodiments, by vapor deposition of molecules, or in some embodiments, by dielectrophoresis (DEP), which attracts molecules to the gap.

Once a molecule resides in or on the gap, the electrical response of the molecule can be measured using the pair of electrodes. In some embodiments, an electrical parameter analyzer can be contacted to contact pads which are connected to the electrodes. According to this aspect, and in some embodiments, the parameter analyzer can generate and record signals such as voltage and current. The parameter analyzer can supply voltage to the device, and record changes in current. The current/voltage (I/V) curve can be used to assess the electrical response of the molecule or of the molecular aggregates. A computer program may be used to calculate conductance and to plot conductance versus voltage applied.

According to this aspect, and in some embodiments, when the device is fabricated on a conductive substrate covered by an insulating layer, a gate voltage can be applied to the device. The current as a function of the gate voltage may be measured, and 3D conductance maps can be drawn, further characterizing the gap and its content.

According to this aspect, and in some embodiments, an additional electrode(s) can be placed in the vicinity of the nanogap, when the electromigration process is conducted on a thin T-junction or a thin cross (X) shaped conducting wire. A three- or four-electrode configuration can be used to further probe the molecule in the gap, and to construct novel devices for molecular electronics. Such devices may comprise molecules that function as electronic components.

According to this aspect, and in some embodiments, the electronic components mimicked by the molecules can be resistors, capacitors and logic gates. The incorporation of nanoparticles in the gap is used to construct electronic devices that utilize such geometry, for example single-electron transistors and devices relying on the coulomb blockade phenomenon.

Example 3

Nanoparticle Size Distribution Determination

A nanogap device is constructed with a large array of electrode pairs, for example as described in Example 1. Voltage conditions are controlled such that the gap in each electrode pair or in each series of electrode pairs differ from another electrode pair or pairs in the array. The difference in gap size may be controlled and varied with accurate increments of, for example, 0.5 nm. Each electrode pair may be individually addressed by a voltage source and a current analyzer. A series of conducting nanoparticles having a desired size distribution may be introduced to the device from solution. The particles are coated with a functional group that promotes binding to the gap between the electrodes. The number of electrical junctions shortened by the binding of the particles is measured, and the gap size of each shortened junction is recorded. The distribution of shortened junctions and their sizes is used to evaluate the size distribution of the particle population.

Example 4

Chemical Sensing

An embodiment of a nanogap device suitable for chemical sensing is constructed as described herein. A large array of electrode pairs comprising an insulated portion, and a nanogap with non-insulated electrode portions located proximally thereto is patterned on a substrate. Each electrode pair according to this embodiment is connected through contact pads to an electrical parameter analyzer system that can supply voltage and can read electrical signals off the electrode pairs. The electrode surface at the nanogap area is modified with functional groups specifically binding to a molecule of interest. The substrate comprising electrodes is exposed to a gaseous or a liquid sample containing a molecule. Upon binding of the molecule to the electrode pair and its containment therefore within the nanogap, the electrical response is changed due to the electronic properties of the molecule. Molecules that undergo a distinct electrochemical reaction can therefore be detected.

Example 5

Biosensors

A nanogap device is constructed, for example as described herein. A large array of electrode pairs comprising an insulated portion, and a nanogap with non-insulated electrode portions located proximally thereto is patterned on a substrate. Each electrode pair according to this embodiment is connected through contact pads to an electrical parameter analyzer system that can supply voltage and can read electrical signals off the electrode pairs. The substrate is exposed to a liquid solution or dispersion comprising functionalized nanoparticles. The nanoparticles are functionalized with a molecule that binds to exposed regions of the electrodes, thus nanoparticles are contained within the nanogap, such that they bridge the two electrodes. The nanoparticles may further comprise a binding moiety such as a vector, a reporter, an enzyme, an antibody, etc. The device is exposed to a solution comprising a molecule of interest. Upon binding of the molecule of interest to the binding moiety, the electrical response of the nanogap is changed. The change is the result of interaction between the biological molecule and the binding moiety, thereby changing the electronic configuration of the functionalized nanoparticles. Only biological molecules with distinct binding affinity to the binding moiety will be detected. These molecules can be detected in the presence of other not-binding molecules.

Example 6

Electrochemical Catalysis of Chemical and Biological Processes

In some embodiments, the device of the present invention can be used to electrochemically catalyze reactions. In some embodiments an array of nanogaps within electrode pairs are subjected to a molecular solution. The surface of the electrodes near the gap are designed such that they can bind a molecule of interest from solution. Some molecules will bridge the gap between the electrodes. An electrical perturbation such as an AC or DC voltage or an AC coupled with a DC voltage will be applied to the nanojunction in solution. The insulation of a large part of the electrode prevents background currents and reaction from masking the desired process. The electrical perturbation causes a change of the electronic configuration of the molecule that can catalyze molecular events such as the bond breaking, ion release or ion binding, conformational change that can lead to the release or binding of a molecule from solution, bond formation between the trapped molecule and molecules from solution, photon release from the molecule, or a chemical reaction between the molecule and the substrate onto which the junction is set. Such catalysis has the advantage of localization. It has the advantage of qualitative control over the reaction, and the products, since the selective trapping and selective electrical pulses applied are highly process-specific. This method has the advantage of quantitative control over the reaction as the number of reaction sites are known, and each junction can be independently addressed.

Example 7

Self-Aligned Selectively Insulated Nanogap Devices for Biosensing Application An embodiment of a self-aligned process to fabricate selectively insulated nanogap devices for biosensing application was performed. A thin PMMA layer was spun on fabricated gold electrode with a constriction. When applying a slow voltage sweep till the electrode break down, there was simultaneous hole formation in PMMA layer and nanogap formation in gold electrode. This self-aligned process provided selectively insulated nanogap devices, which could significantly reduce the ionic conduction from electrolyte in biosensing. The mechanism of the hole formation in the PMMA layer was heat induced evaporation. This proposed mechanism has been proven by in situ AFM and laser annealing simulation.

Fabrication

Figure 12:
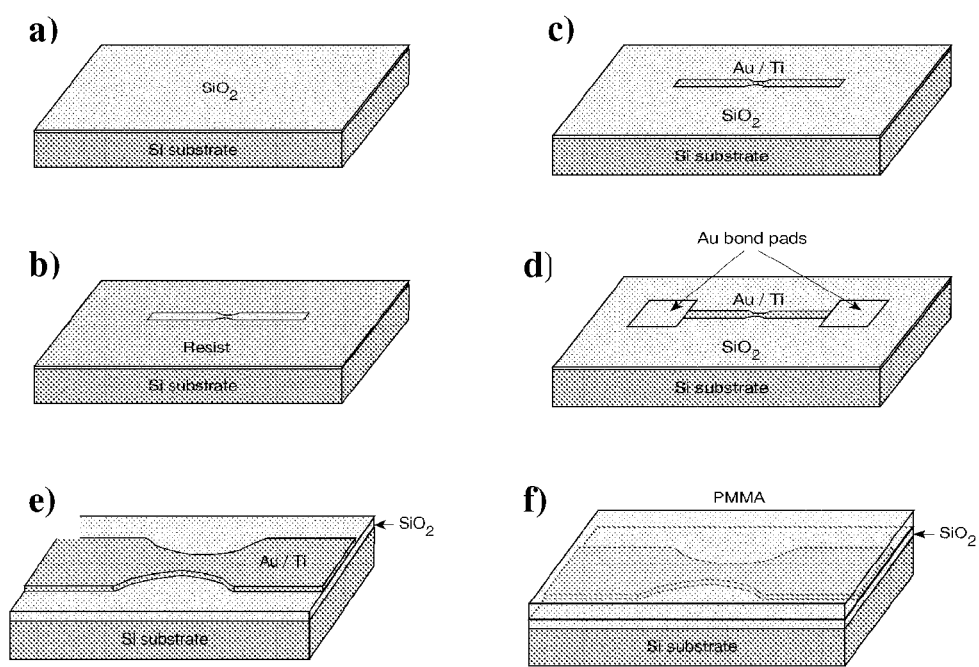
FIG. 12 depicts a schematic diagram of process flow of an embodiment of device fabrication: a) bare substrate: $SiO_2$ (500 nm)/Si substrate; b) butterfly structure patterned by EBL; c) gold electrode after evaporation and lift-off; d) contact pads patterned by optical lithography; e) details at the constriction; f) spin with PMMA layer.

A schematic diagram of process to illustrate the fabrication of the insulating protected nanogap device is shown in FIG. 12. The die was patterned in order to define the electrode with a weak junction, called butterfly structure, by electron beam lithography using polymethylmethacrylate (PMMA) resist (FIG. 12a). A metal layer of 18 nm-thick gold and 1.5 nm-thick Ti (as adhesion layer) was thermally evaporated (BOC Edwards, Auto 306 Vacuum Evaporator) to the resist-patterned die and lifted-off in acetone, to define the gold electrode (FIG. 12b). This was followed by optical lithography using AZ5212 photoresist to define large contact pads (400 um×400 um) (FIG. 12c). A second layer of 150 nm-thick gold and 15 nm Ti was thermally evaporated and lifted-off to deposit the contact pads (FIG. 12d). An insulating polymer layer, in this case PMMA was used, was spun to cover the whole device (FIG. 12f). Next, the die is bonded on a 24-pin Standard IC package and ready for self-aligned nanogap and insulating hole formation.

Result and Discussion

Figure 13:
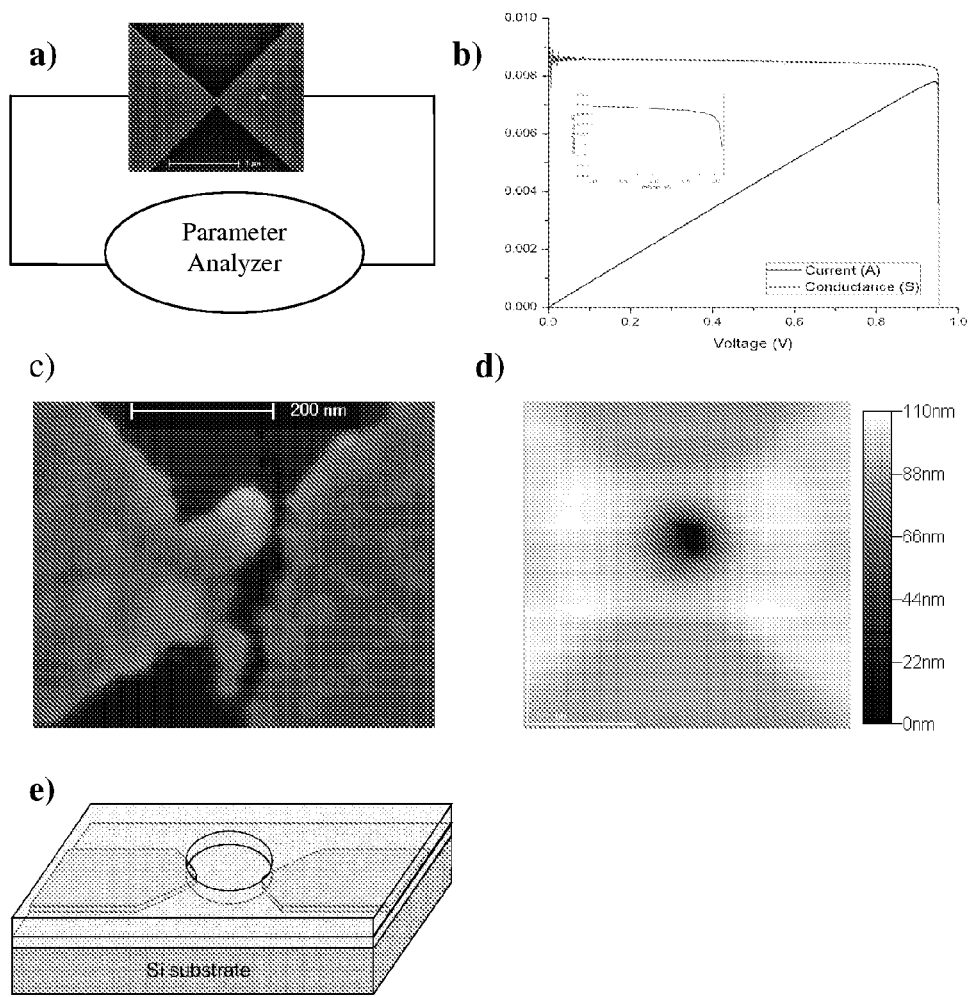
FIG. 13 depicts a) a schematic drawing of an embodiment of a circuit; b) a typical IV curve as a function of V (time). 1V corresponds to 7000 s; c) SEM picture of resulted nanogap; d) topographical picture of a selectively insulated nanogap device by AFM. The hole is ~150 nm in diameter; e) schematic drawing of an embodiment of a selectively insulated nanogap device.

A simple voltage sweep using 1 mV steps at intervals of 7 seconds was applied to the butterfly structure at room temperature using a Keithley4200 parameter analyzer. (FIG. 13a). The default ramp rate of a voltage sweep in the parameter analyzer is 50ms. As mentioned before, a normal voltage sweep could trigger the electromigration in the electrode, but the joule heating would lead to fast temperature rise and cause uncontrollable thermal runaway or local melting of the materials, and inevitably lead to large gaps in the electrode. Using a slower ramp rate allows the local temperature of the weak junction to be more controllable and hence leads to nanogap formation. Experiments showed that an interval of 3 seconds and more would create a gap with sub-um size. In this paper, gaps are formed by intervals of 7 seconds. A typical I-V curve is shown in FIG. 13b). The resulted nanogap was examined in scanning electron microscope (SEM) and shown in FIG. 13c). FIG. 13d) is a topographical picture obtained by atomic force microscope (AFM) of a selectively insulated nanogap device. The schematic drawing of a final device is shown in FIG. 13e).

When a voltage is applied to the electrode, the current density at the constriction is highest for the smallest cross section area. Hence, electromigration of gold atoms there will occur as responding to the momentum carrying electrons. Eventually, the constriction becomes a nanogap by electromigration.

Simultaneously, the insulating polymer is heated up by joule heating ($P=I^2R$). The local temperature of constriction of gold electromigration before breakdown is as high as 450K, and the boiling temperature of PMMA is 473K. The polymer at the constriction is heated the most due to the highest resistance, and locally evaporates and form a self-aligned hole right at the position of the nanogap.

Figure 14:
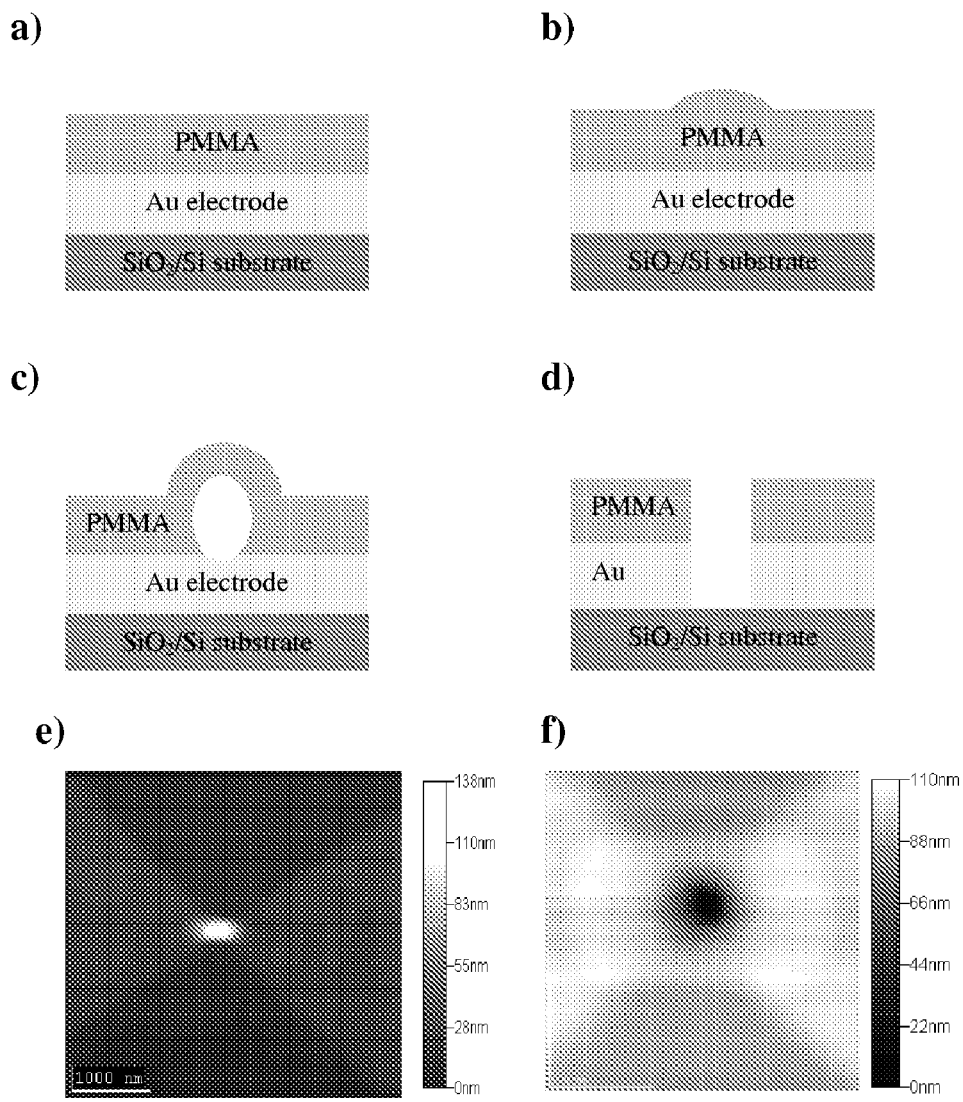
FIG. 14: a)-d) depicts a schematic drawing of an embodiment of a PMMA hole formation process; e)-f) topographical images of real samples scanned by atomic force microscope (AFM); a) Original plain PMMA layer on gold electrode; b) PMMA starts to expand and reflow at the constriction where heats the most; c) A bubble starts to form as the PMMA near to the gold surface starts to evaporate; d) PMMA eventually evaporates locally and form a hole at the vicinity of the Nanogap; e) A PMMA bubble; f) A PMMA hole.

An embodiment of a possible hole formation mechanism is shown in the schematic in FIG. 14a)-d). Initially the polymer started to reflow, and then the polymer near to the gold surface evaporated first and formed a bubble at the constriction. The PMMA bubble had eventually blew and formed a hole at the constriction. Two topographical images of real samples showing the PMMA bubble and PMMA hole are shown in FIGS. 14e) and 3f).

The volume of the polymer layer for its initial status and the status after electrical treatment was calculated by MATLAB. For the sample in FIG. 14e), the volume calculation shows that there is a volume increment of $4.56 \times 10^7$ nm$^3$, which infers the bubble formation. Meanwhile, for the sample in FIG. 14f), it is shown that there is a volume lost, and hence we believe that there is due to the evaporation of the material. The volume lost of the PMMA layer calculated in MATLAB is $1.84 \times 10^6$ nm$^3$, while for a hole of 150 nm diameter and 100 nm thickness, the volume estimated is $1.77 \times 10^6$ nm$^3$. The two values from experimental calculation and estimation are very close to each other showing the results are quite reliable.

In addition, to prove that the PMMA evaporation is heat induced, a simulation using a laser (532 nm) was carried out. The gold electrode was deposited on a quartz plate, and spun with PMMA. The laser in continuous mode was injected from back to the substrate to heat up the gold electrode and hence the PMMA layer (FIG. 15a). The power of the laser was 4.8 mW. FIG. 15b-f are the resulted PMMA layer topography of heating time 1 min, 2 mins, 3 mins, 4 mins and 5 mins respectively. Gradual topographical change was observed. At first, the PMMA layer reflowed and formed a protrusion (FIG.

15b). And then the polymer locally evaporated (FIGS. 15c, d and e), and eventually formed a hole (FIG. 15f). These topographical changes are consistent with the proposed mechanism of hole formation mechanism. Volume calculation of each image showed a gradual lost of material (table 1), which proved the gradual evaporation of the polymer.

This set of experiments showed that at energy input of 1.44 J (E=Pt), the polymer layer was able to be evaporated away by heating. In the real experiment of selectively insulated nanogap fabrication, the formation of the PMMA hole occurred at the very last minute of voltage sweeping (observed during in situ AFM scanning). The last 20 steps (140 s) of a sample IV record were taken into account for energy calculation, the energy from joule heating $$\left(P = \frac{V^2}{R}\right) \text{ is } E = \sum_{V_1}^{V_2} \frac{V^2}{R} \times \Delta t,$$

where voltage is from 1.28V to 1.30V at 1 mV increment and R=2305 Ω, Δt=7 s. The calculated energy was 1.06 J, which is very close to what was observed in laser annealing experiments. Also, in the formation of self-aligned hole, the process happened in a much faster manner (1 min vs 5 mins), with a much smaller hole (150 nm vs. 1 um diameter hole) and with different power input (increasing vs. uniform). A much more drastic change is expected in real experiments by joule heating and expect the formation of the PMMA bubble.

To further illustrate the hole formation, a continuous AFM scan was carried out to monitor the topographical change of the polymer layer coated on the electrode while applying voltage sweep. Each image scan took 50 seconds. The series of AFM images showed that initially there was no significant change in the polymer layer. FIG. 16a shows the initial polymer layer on the butterfly electrode. FIGS. 16b and 16c shows the image after 60 mins and 135 mins sweeping. Noticeable topographical change only occurred at last two images. The in situ AFM scan revealed that the whole hole formation process took less than 1 min. The final formation of a PMMA hole could be captured.

Applications

The selectively insulated nanogap device can significantly reduce the ionic current from the electrolyte. For example, 0.1M Calcium chloride solution was used to test the ionic current from the electrolyte. The results are shown in FIG. 17. The ionic current tested by a bare nanogap device was two orders of magnitudes higher than the PMMA layer protected nanogap device. The insulating polymer layer has prevented parallel conductions through the electrode. Only the vicinity of the nanogap received the electrical signal from the solution. In this manner, the noise from the electrolyte was greatly suppressed, and hence the signal to noise ratio was increased significantly. This embodiment of the invention is particularly useful for DNA hybridization detection as DNA hybridization is most efficient in highly ionic buffer solution. The selectively insulated nanogap devices are ideal for bacteria sensing in aqueous solution in one embodiment.

In addition, the selectively insulated nanogap were used as a template for incorporation of nano-objects, such as gold nanoparticles (FIG. 18a). It could be also fabricated in a manner of an array form to accommodate different nano-objects selectively (FIG. 18b). FIGS. 18c and 18d are the SEM pictures of an embodiment of selective deposition of gold nanoparticles into the nanogap by dielectrophoresis. Also, direct chemical assembly of gold nanoparticles was shown to be selective by PMMA hole protected nanogap as shown in FIG. 18e, while FIG. 18f shows the direct chemical assembly of gold nanoparticles that was performed without the PMMA hole. 3-aminopropyl triethoxysilane was used as a chemical immobilizer to assemble the gold nanoparticles.

Conclusion

In this example, fabrication of a selective insulated nanogap device was presented. All electrical conducting parts in the nanogap device were covered by an insulating polymer layer except in the vicinity of the gap. This embodiment of the process utilized thermally assisted electromigration of electrode to form a nanogap and heat generated by joule heating for a hole formation in the insulating polymer layer right at the position of the nanogap. The two processes were carried on simultaneously when applying voltage according to this embodiment. The mechanism of hole formation was possibly heat induced evaporation in one embodiment. This has been illustrated and proven by laser heating and in situ AFM. Only signals from nanogap could be read, which increased the signal-to-noise ratio. Experimental results showed that the ionic current is reduced by two orders of magnitudes comparing insulated with no insulating layer protected nanogap device.

Example 8

An Embodiment of Topography and Temperature Effect of Nanogap Structure Formed by Thermally Assist Electromigration In this example a simple technique to fabricate controllable and repeatable sub 10-nm gold nanogap devices is presented. This is done by using a voltage sweep method that does not require any sophisticated software or cryogenic temperature. It was observed the nanogap invariably formed on the cathode side and this was accompanied by hillock formation on the anode side. The mechanism that gave rise to this topography was discussed, and the temperature effect on where the nanogap and the hillocks were formed was also investigated. The nanogap devices could be used for label-free DNA hybridization detection.

1. Fabrication

A schematic illustrating the fabrication of nanogap device on a 500 nm $SiO_2$-insulated silicon substrate is shown in FIG. 19. Electrodes with a constriction, a so-called butterfly (or bow-tie) structure, were defined by electron beam lithography using polymethylmethacrylate (PMMA) resist (FIG. 19b). A metal layer of 2 nm-thick Ti (as adhesion layer) and 18 nm-thick gold was thermally evaporated (BOC Edwards, Auto 306 Vacuum Evaporator) on the resist-patterned die and lifted-off in acetone, to create the gold electrode (FIG. 19c). This was followed by optical lithography using AZ5212 photoresist to define large contact pads (400 um×400 um). A second layer of 15 nm Ti and 150 nm-thick gold was thermally evaporated and lifted-off to deposit the contact pads (FIG. 19d). Next, the die was bonded on a 24-pin DIP IC package and ready for nanogap formation.

A simple voltage sweep using 1 mV steps at intervals of 7 seconds was applied to the butterfly structure at room temperature using a Keithley4200 parameter analyzer. (FIG. 20a). The default ramp rate of a voltage sweep in the parameter analyzer is 50 ms. A normal voltage sweep could trigger the electromigration in the electrode, but the joule heating would lead to fast temperature rise and cause uncontrollable thermal runaway or local melting of the materials, and inevitably lead to large gaps in the electrode. Using a slower ramp rate allowed the local temperature of the weak junction to be more controllable and hence leads to nanogap formation. Experiments showed that an interval of 3 seconds and more would create a gap with sub-μm size. In this example, gaps were formed by intervals of 7 seconds. A typical I-V curve is shown in FIG. 20b).

2. Results and Discussion

Gaps with tunneling current ranging from $10^{-10}$ A to $10^{-8}$ A at 1V measured at room temperature and in air were obtained. The current tunneling through a metal-vacuum-metal gap I(V)

$$\Box \exp\left(-2\sqrt{\frac{2m(\Phi - V)}{\eta^2}}d\right),$$

, where d is the gap distance, V is the applied voltage, and Φ is the work function of the gold electrodes. For example, for a gap having 1 nA tunneling current at 1V, the gap is 1.2 nm wide. The dimensions and reproducibility of gaps obtained were comparably good to what have been published about nanogap fabrication using other protocols for thermally assisted electromigration. The experimental setup shown in this embodiment is much simpler and easier than other electromigration schemes.

It was observed that for gaps fabricated according to this embodiment, the gaps formed at the cathode side rather than right at the narrowest constriction. In addition, it was noticed that there were always bright spots placed symmetrically opposite to the gap location when the sample was viewed in the scanning electron microscope (SEM). These bright spots under SEM suggest surface protrusions that give rise to a higher electron yield. Imaging by atomic force microscopy (AFM) further confirmed that there was hillock formation symmetrically to the gap location, on the anode side. The formation of hillocks may have been the result from gold atom migration from the cathode side.

Due to the very nature of the butterfly structure, there possibly was current crowding around the constriction. Hence, the temperature was probably highest at the constriction due to Joule heating and drop off in both directions. As the electromigration flux $$J \propto \exp\left(\frac{-Q}{kT}\right)$$

scales with temperature T, there expected to be a sharp maximum flux at the constriction, where Q is the activation energy for an atom to migrate, k is the Boltzmann's constant. However, the variations of microstructural parameters over a film may cause a nonuniform distribution of atomic flow rate, either a mass depletion (divergence>0) or accumulation (divergence<0), which leads to formation of voids or hillocks, respectively. On the cathode side, a flux divergence goes from slow to fast as the electrode cross area is decreasing, so material is depleted and a tensile stress is created, followed by gradual voids formation, which develops, and finally leads to the formation of a nanogap. On the anode side, a compressive stress develops and hillocks gradually form. Failure occurs at the peak flux divergence so that the locations of the voids and hillocks can be found when |dJ/dx| is maximum or when $d^2J/dx^2$ is zero. Since the structure is symmetric, the location of void and hillock is also symmetric. The schematic in FIG. 22 illustrates the mechanism of formation of the nanogap and gold hillocks.

The influence of ambient temperature on nanogap formation was also studied. As discussed above, the local temperature has a significant effect on the electromigration flux. The location of the hillock/voids is dependent on the shape of the temperature (T) vs. position (x) curve. Changing the ambient temperature will change the shape of the T(x) curve and consequently the J(x) curve, thereby affecting the location of the voids and the hillocks. A set of experiments was carried out in vacuum at different temperatures (room temperature $T_1$, 50° C. $T_2$ and 90° C. $T_3$) using a furnace tube. The vacuum is to eliminate any possible effect resulted from heat convection in air. From FIG. 23, it can be seen that the locations of gap/hillock were further away from the constriction when the ambient temperature was higher. The higher the ambient temperature, the less steep the T(x) curve, and likewise the J(x) curve. The flux density will change more slowly along the length of the electrode. Hence, the location of maximum |dJ/dx| or zero $d^2J/dx^2$ is further away from the constriction. A qualitative sketch of J, dJ/dx and $d^2J/dx^2$ curves at three different temperatures is shown alongside the SEM pictures in FIG. 23.

Our nanogap devices provide label free DNA hybridization detection as shown in FIG. 24. All 20 nm gold nanoparticles and oligonucleotides were purchased from Sigma Aldrich Ltd. The nanogap electrodes were functionalized with a capture DNA, and the gold nanoparticles (Au NP) were functionalized with a probe DNA. With the presence of a complementary DNA (target), the target was hybridized with the capture DNA and the probe DNA. In this case, the target DNA behaved like a linker to immobile the Au NP to the nanogap electrode, as the schematic shown in FIG. 24a). The conductance change of the nanogap caused by Au NP assembly was electrically detected and indicated the occurrence of DNA hybridization. When the hybridization failed, the Au NPs were not able to assemble to the nanogap, and the conductance of the device remained. The SEM picture of Au NP assembled to the nanogap is shown in FIG. 24b). FIG. 24c) shows IV characteristics of a nanogap before and after DNA hybridization. The current increased from tens of pA to a few nA resulted from Au NP assembly.

3. Conclusion

In this example, nanogap devices were fabricated by a simple voltage sweep, which can be done by any source measurement unit. With control of the sweep rate by adjusting delay time of each voltage increment, the thermal runaway of electrode is prevented and sub-10 nm nanogap was obtained. The fabrication method required no sophisticated feedback control or cryogenic environment. In addition, the topography of the resulted electrode was investigated. One embodiment of the mechanism of the location of nanogap and the formation of observed hillocks was explained. Temperature effect has been investigated as well. It was found that the higher the ambient temperature is, the larger the distance between the hillocks and the voids is. The experimental results have proven the proposed mechanism of the formation of nanogap and hillocks according to this embodiment. The nanogap devices were able to detect DNA hybridization by direct assembly of gold nanoparticles. The conductance increment, resulted from DNA hybridization, was clearly detected electrically.

The invention claimed is:

1. A process for preparing a nanogap device for measuring changes in electrical properties or electrical responses of a sub-micron sized material, said device comprising:
    (a) a substrate; and
    (b) at least one conducting electrode pair separated by a nanogap positioned on or within said substrate, wherein
        i. a first portion of said conducting electrode pair comprises an insulator coating; and
        ii. a second portion of said conducting electrode pair proximal to said nanogap does not comprise an insulator coating, said process comprising:

a. positioning a conducting material on a substrate wherein said material has a longitudinal axis which exceeds that of its horizontal axis, wherein said conducting material comprises a second portion of said material along its longitudinal axis, which is thinner than a first portion of said material along its longitudinal axis;

b. applying an insulator coating to said conducting material; and c. applying a voltage to said conducting material;

wherein application of said voltage results in forming a gap in said second portion and at least partial removal of said insulator coating of said second portion.

2. The process of claim 1, wherein application of voltage results in electromigration of atoms occurring after at least partial removal of said insulator coating.

3. The process of claim 1, wherein upon application of voltage the electromigration of atoms and the at least partial removal of said insulator coating are parallel processes.

4. The process of claim 1, wherein said gap formed has a width ranging from 0.5-100 nm.

5. The process of claim 4, wherein said removal of insulator coating results in an uncoated area ranging from 0.01% to 1% of the total area of the conducting material.

6. The process of claim 1, wherein said conducting material is made of gold.

7. The process of claim 1, wherein said conducting material is a conducting wire.

8. The process of claim 1, wherein said insulating coating is PolyMethylMethacrylate (PMMA).

9. The process of claim 1, wherein said substrate is silicon, silicon dioxide or a combination thereof.

10. The process of claim 1, wherein said positioning is of a series of conducting materials on said substrate.

11. The process of claim 1, wherein said device is compatible for use with a liquid or a gas.

12. The process of claim 1, wherein the size of said device, ranges from between 100 nm to 10 cm.

13. The process of claim 1, wherein at least said thin second portion of said conducting material is suspended over the substrate.

14. The process of claim 1, wherein said device is comprised of a biocompatible material.

* * * * *